(12) United States Patent
Gillespie et al.

(10) Patent No.: US 10,208,067 B2
(45) Date of Patent: Feb. 19, 2019

(54) COMPOUNDS FOR TREATING SPINAL MUSCULAR ATROPHY

(71) Applicant: Hoffmann-La Roche Inc., Little Falls, NJ (US)

(72) Inventors: Robert Jack Gillespie, Basel (CH); Hasane Ratni, Habsheim (FR); Jerome Charles Sarie, Basel (CH)

(73) Assignee: HOFFMANN-LA ROCHE INC., Little Falls, NJ (US)

(*) Notice: Subject to any disclaimer, the term of this patent is extended or adjusted under 35 U.S.C. 154(b) by 0 days.

(21) Appl. No.: 15/814,703

(22) Filed: Nov. 16, 2017

(65) Prior Publication Data

US 2018/0194781 A1 Jul. 12, 2018

Related U.S. Application Data

(63) Continuation of application No. PCT/EP2016/060952, filed on May 17, 2016.

(30) Foreign Application Priority Data

May 20, 2015 (EP) .................................... 15168452

(51) Int. Cl.
*C07D 487/22* (2006.01)
*A61K 31/519* (2006.01)
*C07D 519/00* (2006.01)
*A61P 21/00* (2006.01)

(52) U.S. Cl.
CPC .......... *C07D 519/00* (2013.01); *A61K 31/519* (2013.01); *A61P 21/00* (2018.01); *C07D 487/22* (2013.01)

(58) Field of Classification Search
CPC .. C07D 519/00; C07D 487/22; A61K 31/517; A61K 31/519
See application file for complete search history.

(56) References Cited

U.S. PATENT DOCUMENTS

| 2002/0099208 | A1 | 7/2002 | Yu et al. |
| 2017/0197990 | A1* | 7/2017 | Ratni .................. C07D 519/00 |

FOREIGN PATENT DOCUMENTS

| DE | 23 45 064 A1 | 4/1974 |
| WO | 02/062290 A2 | 8/2002 |
| WO | 2005/061513 A1 | 7/2005 |
| WO | 2009/151546 A2 | 12/2009 |
| WO | 2010/019326 A1 | 2/2010 |
| WO | 2013/020993 A1 | 2/2013 |
| WO | 2013/068769 A1 | 5/2013 |
| WO | 2013/119916 A2 | 8/2013 |
| WO | 2014/184163 A1 | 11/2014 |
| WO | 2015/173181 A1 | 11/2015 |
| WO | 2015/110446 A1 | 7/2016 |

OTHER PUBLICATIONS

Morrison, All about spinal muscular atrophy (SMA), retrieved from https://www.medicalnewstoday.com/articles/192245.php on Jun. 20, 2018, p. 1-8. (Year: 2018).*
Combrink et al., "Respiratory syncytial virus fusion inhibitors. Part 6: An examination of the effect of structural variation of the benzimidazol-2-one heterocycle moiety" Bioorganic & Medicinal Chemistry Letters 17(17):4784-4790 (Aug. 4, 2007).
ISR of PCT/EP2012/065499 (Sep. 20, 2012) WO2013/020993.
ISR of PCT/EP2014/059699 (Jul. 10, 2014) WO2014/184163.
ISR of PCT/EP2015/051066 (Feb. 6, 2015) WO2015/110446A1.
ISR of PCT/EP2015/060343 (Jul. 6, 2015) WO2015/173181.
ISR of PCT/EP2016/060952 (Jun. 16, 2016).
Sin et al., "Respiratory syncytial virus fusion inhibitors. Part 7: Structure—activity relationships associated with a series of isatin oximes that demonstrate antiviral activity in vivo" Bioorganic & Medicinal Chemistry Letters 19(16):4857-4862 (Aug. 15, 2009).

* cited by examiner

*Primary Examiner* — Rebecca L Anderson
*Assistant Examiner* — Karen Cheng
(74) *Attorney, Agent, or Firm* — Mark D. Kafka; Genentech, Inc.

(57) ABSTRACT

The present invention provides compounds of formula (I)

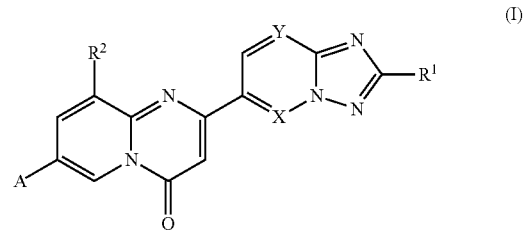

wherein A, X, Y, $R^1$ and $R^2$ are as described herein, as well as pharmaceutically acceptable salts thereof. Further the present invention is concerned with the manufacture of the compounds of formula (I), pharmaceutical compositions comprising them and their use as medicaments.

33 Claims, No Drawings
Specification includes a Sequence Listing.

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaaggaaggt gctcacatt                                                  19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tctttatgtt tttggcgtct tc                                              22

<210> SEQ ID NO 3
<211> LENGTH: 26
<212> TYPE: DNA
<213> ORGANISM: Artificial Sequence
<220> FEATURE:
```

-continued

<223> OTHER INFORMATION: Description of Artificial Sequence: Synthetic
      probe

<400> SEQUENCE: 3
aaggagaaat gctggcatag agcagc                                        26

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cgcctggtca ccagggctgc t                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caacggattt ggtcgtattg g                                             21

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgatggcaac aatatccact ttacc                                         25

COMPOUNDS FOR TREATING SPINAL MUSCULAR ATROPHY

CROSS-REFERENCE TO RELATED APPLICATIONS

This application is a continuation of, and claims priority to, International Patent Application No. PCT/EP2016/060952, filed on May 17, 2016. This application also claims priority to European Patent Application No. 15168452.9, filed on May 20, 2015. The entire contents of each of the above patent applications are hereby incorporated by reference.

SEQUENCE LISTING

The instant application contains a Sequence Listing which has been submitted electronically in ASCII format and is hereby incorporated by reference in its entirety. Said ASCII copy, created on Feb. 16, 2018, is named P32752-US_SL.txt and is 1,671 bytes in size.

INTRODUCTION

The present invention provides compounds which are SMN2 gene splicing modulators, their manufacture, pharmaceutical compositions comprising them and their use as medicaments for the treatment of SMN-deficiency-related conditions, particularly for the treatment of spinal muscular atrophy (SMA).

In particular, the present invention relates to compounds of formula (I)

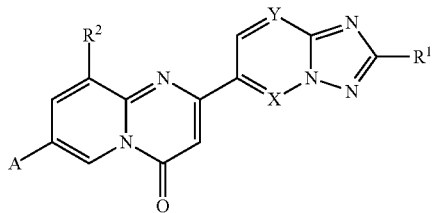

(I)

wherein X, Y, A, $R^1$ and $R^2$ are as described herein, or pharmaceutically acceptable salts thereof.

BACKGROUND

Spinal muscular atrophy (SMA), in its broadest sense, describes a collection of inherited and acquired central nervous system (CNS) diseases characterized by progressive motor neuron loss in the spinal cord and brainstem causing muscle weakness and muscle atrophy. The most common form of SMA is caused by mutations in the Survival of Motor Neuron (SMN) gene and manifests over a wide range of severity affecting infants through adults (Crawford and Pardo, *Neurobiol. Dis.*, 1996, 3:97).

Infantile SMA is the most severe form of this neurodegenerative disorder. Symptoms include muscle weakness, poor muscle tone, weak cry, limpness or a tendency to flop, difficulty sucking or swallowing, accumulation of secretions in the lungs or throat, feeding difficulties, and increased susceptibility to respiratory tract infections. The legs tend to be weaker than the arms and developmental milestones, such as lifting the head or sitting up, cannot be reached. In general, the earlier the symptoms appear, the shorter the lifespan. As the motor neuron cells deteriorate, symptoms appear shortly afterward. The severe forms of the disease are fatal and all forms have no known cure. Infants with a severe form of SMA frequently succumb to respiratory disease due to weakness in the muscles that support breathing. Individuals with milder forms of SMA live much longer, although they may need extensive medical support, especially those at the more severe end of the spectrum. The clinical spectrum of SMA disorders has been divided into the following five groups.

(a) Type 0 SMA (In utero SMA) is the most severe form of the disease and begins before birth. Usually, the first symptom of Type 0 SMA is reduced movement of the fetus that can first be observed between 30 and 36 weeks of pregnancy. After birth, these newborns have little movement and have difficulties with swallowing and breathing.

(b) Type 1 SMA (Infantile SMA or Werdnig-Hoffmann disease) presents symptoms between 0 and 6 months. form of SMA is also very severe. Patients never achieve the ability to sit, and death usually occurs within the first 2 years without ventilatory support.

(c) Type 2 SMA (Intermediate SMA) has an age of onset at 7-18 months. Patients achieve the ability to sit unsupported, but never stand or walk unaided. Prognosis in this group is largely dependent on the degree of respiratory involvement.

(d) Type 3 SMA (Juvenile SMA or Kugelberg-Welander disease) is generally diagnosed after 18 months. Type 3 SMA individuals are able to walk independently at some point during their disease course but often become wheelchair-bound during youth or adulthood.

(e) Type 4 SMA (Adult onset SMA). Weakness usually begins in late adolescence in the tongue, hands, or feet, then progresses to other areas of the body. The course of adult SMA is much slower and has little or no impact on life expectancy.

The SMN gene has been mapped by linkage analysis to a complex region in chromosome 5q (Lefebvre S. et al., *Cell* (1995) 80:155). In humans, this region contains an approximately 500 thousand base pairs (kb) inverted duplication resulting in two nearly identical copies of the SMN gene. SMA is caused by an inactivating mutation or deletion of the telomeric copy of the gene (SMN1) on both chromosomes, resulting in the loss of SMN1 gene function. However, all patients retain the centromeric copy of the gene (SMN2), and the copy number of the SMN2 gene in SMA patients generally correlates inversely with the disease severity; i.e., patients with less severe SMA have more copies of SMN2. SMN2 pre-mRNA undergoes alternative splicing of exon 7 caused by a translationally silent C to T mutation in exon 7. As a result, the majority of transcripts produced from SMN2 lack exon 7 (Δ7 SMN2), and encode a truncated SMN protein that has an impaired function and is rapidly degraded.

The SMN protein plays a role in RNA processing and metabolism, having a well characterized function of mediating the assembly of a specific class of RNA-protein complexes termed snRNPs. SMN may have other functions in motor neurons, however its role in preventing the selective degeneration of motor neurons is not well established.

In most cases, SMA is diagnosed based on clinical symptoms and by the complete absence of exon 7 of SMN1 gene. However, in approximately 5% of cases SMA is caused by mutation in genes other than the inactivation of SMN 1, some known and others not yet defined. In some cases, when the SMN 1 gene test is not feasible or does not show any abnormality, other tests such as an electromyography (EMG) or muscle biopsy may be indicated.

Medical care for SMA patients at present is limited to supportive therapy including respiratory, nutritional and rehabilitation care; there is no drug known to address the underlying cause of the disease. Current treatment for SMA consists of prevention and management of the secondary effects of chronic motor unit loss. The major management issue in Type 1 SMA is the prevention and early treatment of pulmonary problems, which are the cause of death in the majority of the cases. While some infants afflicted with SMA grow to be adults, those with Type 1 SMA have a life expectancy of less than two years.

Several mouse models of SMA have been developed. In particular, the SMN delta exon 7 (Δ7 SMN) model (Le et al., *Hum. Mol. Genet.*, 2005, 14:845) carries both the SMN2 gene and several copies of the Δ7 SMN2 cDNA and recapitulates many of the phenotypic features of Type 1 SMA. The Δ7 SMN model can be used for both SMN2 expression studies as well as the evaluation of motor function and survival. The C/C-allele mouse model (Jackson Laboratory strain #008714, The Jackson Laboratory, Bar Harbor, Me.) provides a less severe SMA disease model but does not have an overt muscle weakness. This mouse model has the murine Smn1 gene inactivated and carries both the complete SMN2 gene and a hybrid mSmn1-SMN2 gene that undergoes alternative splicing. C/C-allele mice have reduced levels of both SMN2 full length (FL SMN2) mRNA and SMN protein. The C/C-allele mouse model is used for SMN2 expression studies.

As a result of improved understanding of the genetic basis and pathophysiology of SMA, several strategies for treatment have been explored, but none have yet demonstrated success in the clinic.

Gene replacement of SMN1, using viral delivery vectors, and cell replacement, using differentiated SMN1$^{+/+}$ stem cells, have demonstrated efficacy in animal models of SMA. More research is needed to determine the safety and immune response and to address the requirement for the initiation of treatment at the neonatal stage before these approaches can be applied to humans.

Correction of alternative splicing of SMN2 in cultured cells has also been achieved using synthetic nucleic acids: (i) antisense oligonucleotides that target sequence elements in SMN2 pre-mRNA and shift the outcome of the splicing reaction toward the generation of full length SMN2 mRNA (Passini et al., *Sci. Transl. Med.*, 2011, 3: 72ra18; and, Hua et al., *Nature*, 2011, 478:123) and (ii) trans-splicing RNA molecules that provide a fully functional RNA sequence that replace the mutant fragment during splicing and generate a full length SMN1 mRNA (Coady and Lorson, *J Neurosci.*, 2010, 30:126).

Other approaches under exploration include searching for drugs that increase SMN levels, enhance residual SMN function, or compensate for its reduced levels. Aminoglycosides have been shown to enhance the expression of a stabilized extended Δ7 SMN protein produced from Δ7 SMN2 mRNA by promoting the translational read-through of the aberrant stop codon, but have poor central nervous system penetration and are toxic after repeat dosing.

Chemotherapeutic agents, such as aclarubicin, have been shown to increase SMN protein in cell culture; however, the toxicity profile of these drugs prohibits long-term use in SMA patients. Some drugs under clinical investigation for the treatment of SMA include transcription activators such as histone deacetylase (HDAC) inhibitors (e.g., butyrates, valproic acid, and hydroxyurea), and mRNA stabilizers (mRNA decapping inhibitor RG3039 from Pfizer), the goal being to increase the amount of total RNA transcribed from the SMN2 gene. However, the use of the HDAC inhibitors or mRNA stabilizers does not address the underlying cause of SMA and may result in a global increase in transcription and gene expression with potential safety problems in humans.

In an alternative approach, neuroprotective agents such as Olesoxime have been chosen for investigation. Such strategies are not aimed at SMN for the treatment of SMA, but instead are being explored to protect the SMN-deficient motor neurons from neurodegeneration.

A system designed for identifying compounds that increase the inclusion of exon 7 of SMN into RNA transcribed from the SMN2 gene and certain benzooxazole and benzoisoxazole compounds identified thereby have been described in International Patent Application WO2009/151546A1. A system designed for identifying compounds that cause ribosomal frameshifting to produce a stabilized SMN protein from Δ7 SMN2 mRNA and certain isoindolinone compounds identified thereby have been described in International Patent Applications WO2010/019236A1 and WO2013/119916A2.

Despite the progress made in understanding the genetic basis and pathophysiology of SMA, there remains a need to identify compounds that alter the course of spinal muscular atrophy, one of the most devastating childhood neurological diseases.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkylaryl", "haloalkylheteroaryl", "arylalkylheterocycloalkyl", or "alkoxyalkyl". The last member of the combination is the radical which is binding to the rest of the molecule. The other members of the combination are attached to the binding radical in reversed order in respect of the literal sequence, e.g. the combination $C_{1-7}$-alkoxy-heterocycloalkyl refers to a heterocycloalkyl which is substituted by $C_{1-7}$-alkoxy.

The term "moiety" refers to an atom or group of chemically bonded atoms that is attached to another atom or molecule by one or more chemical bonds thereby forming part of a molecule.

For example, the variables A, $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The terms "optional" or "optionally" denote that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The terms "compound(s) of this invention" and "compound(s) of the present invention" refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulae.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid. Particular pharmaceutically acceptable salts of the present invention are salts formed with hydrochloric acid yielding a hydrochloride, dihydrochloride, or trihydrochloride salt, more particularly, a hydrochloride salt.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of the present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The terms "halo", "halogen", and "halide" are used interchangeably herein and denote fluoro, chloro, bromo, or iodo. Particular examples of halogen are fluoro and bromo, most particularly fluoro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples for alkyl are methyl and ethyl.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl and the like. The term "perhaloalkyl" denotes an alkyl group where all hydrogen atoms of the alkyl group have been replaced by the same or different halogen atoms. Particular examples of haloalkyl are trifluoromethyl and difluoromethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy are methoxy and ethoxy.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S. In analogy, the term "tricyclic ring system" denotes three rings which are fused to each other as described for bicyclic ring systems.

The term "cycloalkyl" denotes a saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. One particular example of cycloalkyl is cyclopropyl.

The term "heterocycloalkyl" denotes a saturated or partly unsaturated mono-, bi- or tricyclic ring system of 3 to 10 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples of a partly unsaturated heterocycloalkyl are dihydrofuryl, imidazolinyl, dihydro-oxazolyl, tetrahydro-pyridinyl, or dihydropyranyl. Particular examples of heterocycloalkyl are azetidinyl, oxetanyl, pyrrolidinyl, piperidyl, piperazinyl, 1,4-diazepanyl, 2,6-diazaspiro[3.3]heptanyl, 2,7-diazaspiro[3.4]octanyl, 2,7-diazaspiro[3.5]nonanyl, 3,6-diazabicyclo[3.2.0]heptanyl, 1,3,3a,4,6,6a-hexahydropyrrolo[3,4-c]pyrrolyl, and hexahydro-1H-cyclobuta[1,2-c:1,4-c']dipyrrolyl.

The term "N-heterocycloalkyl" denotes a heterocycloalkyl radical containing at least one nitrogen ring atom and where the point of attachment of the heterocycloalkyl radical to the rest of the molecule is through a nitrogen ring atom. Particular examples of N-heterocycloalkyl are pyrrolidinyl, piperidyl, piperazinyl, 1,4-diazepanyl, 2,6-diazaspiro[3.3]heptanyl, 2,7-diazaspiro[3.4]octanyl, 2,7-diazaspiro[3.5]nonanyl, 3,6-diazabicyclo[3.2.0]heptanyl, 1,3,3a,4,6,6a-hexahydropyrrolo[3,4-c]pyrrolyl, and hexahydro-1H-cyclobuta[1,2-c:1,4-c']dipyrrolyl. More particular examples of N-heterocycloalkyl are pyrrolidinyl, piperazinyl, 2,6-diazaspiro[3.3]heptanyl, 2,7-diazaspiro[3.5]nonanyl, 1,3,3a,4,6,6a-hexahydropyrrolo[3,4-c]pyrrolyl, and hexahydro-1H-cyclobuta[1,2-c:1,4-c']dipyrrolyl.

The term "basicity" in reference to a compound is expressed herein by the negative decadic logarithm of the acidity constant of the conjugate acid (pKa=−log Ka). The larger the pKa of the conjugate acid, the stronger the base (pKa+pKb=14). In this application, an atom or functional group is denoted "basic" if it is suitable to accept a proton and if the calculated pKa of its conjugate acid is at least 7, more particularly if the calculated pKa of its conjugate acid is at least 7.8, most particularly if the calculated pKa of its conjugate acid is at least 8. pKa values were calculated in-silico as described in F. Milletti et al., *J. Chem. Inf. Model* (2007) 47:2172-2181.

The term "alkylene" denotes a linear saturated divalent hydrocarbon group of 1 to 7 carbon atoms or a divalent branched saturated hydrocarbon group of 3 to 7 carbon atoms. Examples of alkylene groups include methylene, ethylene, propylene, 2-methylpropylene, butylene, 2-ethylbutylene, pentylene, hexylene. Particular examples for alkylene are ethylene, propylene, and butylene.

The term "amino" denotes a group of the formula —NR'R" wherein R' and R" are independently hydrogen, alkyl, alkoxy, cycloalkyl, heterocycloalkyl, aryl, heteroaryl or as described herein. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is a group other than hydrogen. The term "tertiary amino" denotes a group wherein both R' and R" are other than hydrogen. Particular secondary and tertiary amines are methylamine, ethylamine, propylamine, isopropylamine, phenylamine, benzylamine, dimethylamine, diethylamine, dipropylamine and diisopropylamine.

The term "protecting group" denotes the group which selectively blocks a reactive site in a multifunctional compound such that a chemical reaction can be carried out selectively at another unprotected reactive site in the meaning conventionally associated with it in synthetic chemistry.

Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting group.

The terms "deprotection" or "deprotecting" denote the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgment of the attending medical or veterinary practitioner, and other factors.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

The term "SMN-deficiency-related conditions" comprises spinal muscular atrophy (SMA) neurogenic congenital arthrogryposis multiplex congenita (AMC), amyotrophic lateral sclerosis (ALS). The term "spinal muscular atrophy" (or SMA) relates to a disease caused by an inactivating mutation or deletion in the SMN1 gene on both chromosomes, resulting in a loss of SMN1 gene function.

Symptoms of SMA include muscle weakness, poor muscle tone, weak cry, weak cough, limpness or a tendency to flop, difficulty sucking or swallowing, difficulty breathing, accumulation of secretions in the lungs or throat, clenched fists with sweaty hand, flickering/vibrating of the tongue, head often tilted to one side, even when lying down, legs that tend to be weaker than the arms, legs frequently assuming a "frog legs" position, feeding difficulties, increased susceptibility to respiratory tract infections, bowel/bladder weakness, lower-than-normal weight, inability to sit without support, failure to walk, failure to crawl, and hypotonia, areflexia, and multiple congenital contractures (arthrogryposis) associated with loss of anterior horn cells.

The term "treating spinal muscular atrophy (SMA)" or "treatment of spinal muscular atrophy (SMA)" includes one or more of the following effects: (i) reduction or amelioration of the severity of SMA; (ii) delay of the onset of SMA; (iii) inhibition of the progression of SMA; (iv) reduction of hospitalization of a subject; (v) reduction of hospitalization length for a subject; (vi) increase of the survival of a subject; (vii) improvement of the quality of life of a subject; (viii) reduction of the number of symptoms associated with SMA; (ix) reduction of or amelioration of the severity of one or more symptoms associated with SMA; (x) reduction of the duration of a symptom associated with SMA; (xi) prevention of the recurrence of a symptom associated with SMA; (xii) inhibition of the development or onset of a symptom of SMA; and/or (xiii) inhibition of the progression of a symptom associated with SMA.

More particular, the term "treating SMA" denotes one or more of the following beneficial effects: (i) a reduction in the loss of muscle strength; (ii) an increase in muscle strength; (iii) a reduction in muscle atrophy; (iv) a reduction in the loss of motor function; (v) an increase in motor neurons; (vii) a reduction in the loss of motor neurons; (viii) protection of SMN deficient motor neurons from degeneration; (ix) an increase in motor function; (x) an increase in pulmonary function; and/or (xi) a reduction in the loss of pulmonary function.

In further detail, the term "treating SMA" refers to the functional ability or retention of the functional ability for a human infant or a human toddler to sit up unaided or for a human infant, a human toddler, a human child or a human adult to stand up unaided, to walk unaided, to run unaided, to breathe unaided, to turn during sleep unaided, or to swallow unaided.

The term "preventing" or "prevention" of a disease state denotes causing the clinical symptoms of the disease state not to develop in a subject that can be exposed to or predisposed to the disease state, but does not yet experience or display symptoms of the disease state.

The term "$EC_{1-5x}$ concentration for production of full length SMN2 minigene mRNA" (or "$EC_{1-5x}$ minigene") is defined as that concentration of test compound that is effective in increasing the amount of full length SMN2 minigene mRNA to a level 1.5-fold greater relative to that in vehicle-treated cells.

The term "$EC_{1-5x}$ concentration for SMN protein expression" (or "$EC_{1-5x}$ SMN protein") is defined as that concentration of test compound that is effective in producing 1.5 times the amount of SMN protein in an SMA patient fibroblast cell compared to the amount produced from the vehicle control.

In detail, the present invention relates to compounds of formula (I)

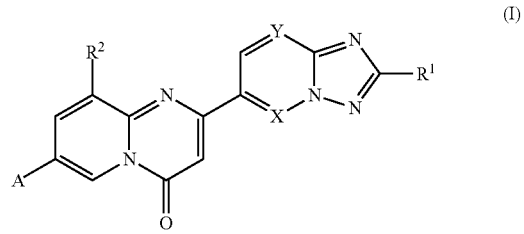

wherein
X is N and Y is $CR^3$ or X is $CR^4$ and Y is N;
$R^1$ is selected from hydrogen, cyano, halo, $C_{1-7}$-alkyl, $C_{1-7}$-haloalkyl, $C_{1-7}$-alkoxy or $C_{3-8}$-cycloalkyl;

R² is selected from hydrogen, cyano, halo, $C_{1-7}$-alkyl, $C_{1-7}$-haloalkyl, $C_{1-7}$-alkoxy or $C_{3-8}$-cycloalkyl;
R³ is selected from hydrogen, cyano, halo, $C_{1-7}$-alkyl, $C_{1-7}$-haloalkyl, $C_{1-7}$-alkoxy or $C_{3-8}$-cycloalkyl;
R⁴ is selected from hydrogen, cyano, halo, $C_{1-7}$-alkyl, $C_{1-7}$-haloalkyl, $C_{1-7}$-alkoxy or $C_{3-8}$-cycloalkyl;
A is N-heterocycloalkyl or NR⁵R⁶, wherein N-heterocycloalkyl comprises 1 or 2 nitrogen ring atoms and is optionally substituted with 1, 2, 3 or 4 substituents selected from R⁷;
R⁵ is heterocycloalkyl comprising 1 nitrogen ring atom, wherein heterocycloalkyl is optionally substituted with 1, 2, 3 or 4 substituents selected from R⁷;
R⁶ is hydrogen, $C_{1-7}$-alkyl or $C_{3-8}$-cycloalkyl;
R⁷ is independently selected from $C_{1-7}$-alkyl, amino, amino-$C_{1-7}$-alkyl, $C_{3-8}$-cycloalkyl, heterocycloalkyl, and heterocycloalkyl-$C_{1-7}$-alkyl or two R⁷ together form $C_{1-7}$-alkylene;
with the proviso that if A is N-heterocycloalkyl comprising only 1 nitrogen ring atom, then at least one R⁷ substituent comprises a basic nitrogen;
or pharmaceutically acceptable salts thereof.

Particular embodiments of the present invention are compounds of formula (I) or pharmaceutically acceptable salts thereof.

Further, it is to be understood that every embodiment relating to a specific X, Y, A, R¹, R², R³, R⁴, R⁵, R⁶, or R⁷ as disclosed herein may be combined with any other embodiment relating to another X, Y, A, R¹, R², R³, R⁴, R⁵, R⁶, or R⁷ as disclosed herein.

A particular embodiment of the present invention relates to compounds of formula (I) wherein
X is N and Y is CR³ or X is CR⁴ and Y is N;
R¹ is $C_{1-7}$-alkyl;
R² is hydrogen or $C_{1-7}$-alkyl;
R³ is hydrogen;
R⁴ is hydrogen;
A is N-heterocycloalkyl, wherein N-heterocycloalkyl comprises 1 or 2 nitrogen ring atoms and is optionally substituted with 1 or 2 substituents selected from R⁷;
R⁷ is independently selected from $C_{1-7}$-alkyl, amino, heterocycloalkyl, and heterocycloalkyl-$C_{1-7}$-alkyl, or two R⁷ together form $C_{1-7}$-alkylene;
with the proviso that if A is N-heterocycloalkyl comprising only 1 nitrogen ring atom, then at least one R⁷ substituent comprises a basic nitrogen;
or pharmaceutically acceptable salts thereof.

A particular embodiment of the present invention relates to compounds of formula (I), wherein X is N and Y is CR³, particularly X is N and Y is CH.

A particular embodiment of the present invention relates to compounds of formula (I), wherein X is CR⁴ and Y is N, particularly X is CH and Y is N.

A particular embodiment of the present invention relates to compounds of formula (I), wherein R¹ is $C_{1-7}$-alkyl, particularly methyl.

In a particular embodiment of the present invention R² is hydrogen or $C_{1-7}$-alkyl; particularly hydrogen or methyl.

In a particular embodiment of the present invention R² is hydrogen.

In a particular embodiment of the present invention R² is methyl.

A particular embodiment of the present invention relates to compounds of formula (I), wherein R³ is hydrogen.

A particular embodiment of the present invention relates to compounds of formula (I), wherein R⁴ is hydrogen.

A particular embodiment of the present invention relates to compounds of formula (I')

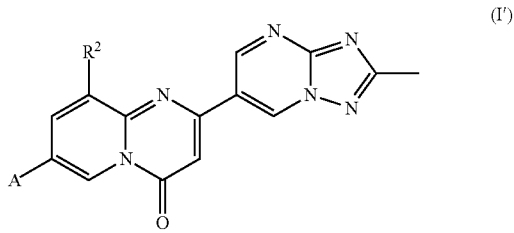

wherein A and R² are as described herein; or pharmaceutically acceptable salts thereof.

A particular embodiment of the present invention relates to compounds of formula (I")

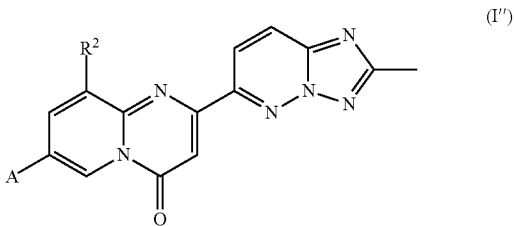

wherein A and R² are as described herein; or pharmaceutically acceptable salts thereof.

A particular embodiment of the present invention relates to compounds of formula (I), wherein A is a saturated mono-, bi- or tricyclic N-heterocycloalkyl comprising 1 or 2 nitrogen atoms and is optionally substituted with 1, 2, 3 or 4 substituents selected from R⁷.

A particular embodiment of the present invention relates to compounds of formula (I), wherein the N-heterocycloalkyl in A as defined herein is substituted with 1 or 2 substituents selected from R⁷.

A particular embodiment of the present invention relates to compounds of formula (I), wherein the N-heterocycloalkyl in A as defined herein is further characterized in that one ring nitrogen atoms is basic.

A particular embodiment of the present invention relates to compounds of formula (I) as defined herein with the proviso that if A is N-heterocycloalkyl comprising only 1 nitrogen ring atom, then at least one R⁷ substituent is amino, amino-$C_{1-7}$-alkyl, N-heterocycloalkyl, or N-heterocycloalkyl-$C_{1-7}$-alkyl.

A particular embodiment of the present invention relates to compounds of formula (I) as defined herein with the proviso that if A is N-heterocycloalkyl comprising only 1 nitrogen ring atom, then at least one R⁷ substituent is amino or N-heterocycloalkyl-$C_{1-7}$-alkyl.

A particular embodiment of the present invention relates to compounds of formula (I), wherein each R⁷ is independently selected from $C_{1-7}$-alkyl, amino, heterocycloalkyl, and heterocycloalkyl-$C_{1-7}$-alkyl or two R⁷ together form $C_{1-7}$-alkylene.

A particular embodiment of the present invention relates to compounds of formula (I), wherein each R⁷ is independently selected from $C_{1-7}$-alkyl, amino, heterocycloalkyl, and heterocycloalkyl-$C_{1-7}$-alkyl.

A particular embodiment of the present invention relates to compounds of formula (I), wherein two $R^7$ together form $C_{1-7}$-alkylene.

A particular embodiment of the present invention relates to compounds of formula (I), wherein each $R^7$ is independently selected from methyl, ethyl, dimethylamino, azetidinyl, oxetanyl, and —$CH_2$-pyrrolidinyl or two $R^7$ together form ethylene or propylene.

A particular embodiment of the present invention relates to compounds of formula (I), wherein A is selected from:

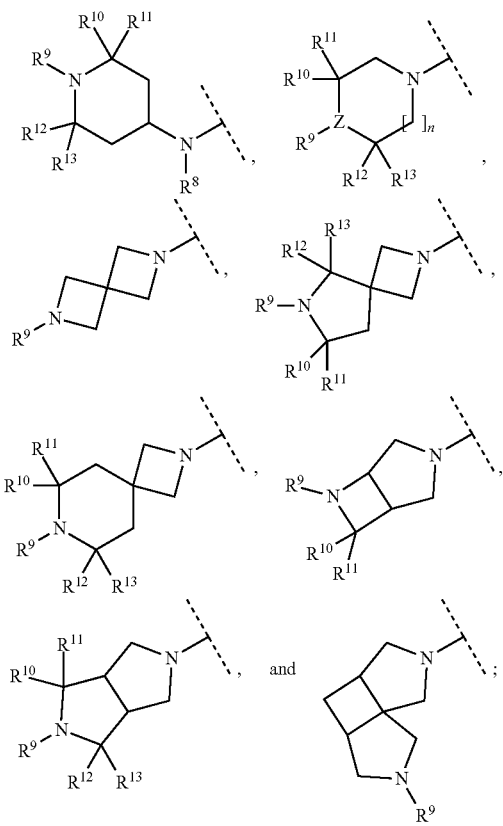

and wherein
Z is N or CH;
$R^8$ is hydrogen, $C_{1-7}$-alkyl or $C_{3-8}$-cycloalkyl;
$R^9$ is hydrogen, $C_{1-7}$-alkyl, amino, heterocycloalkyl, and heterocycloalkyl-$C_{1-7}$-alkyl, or —$(CH_2)_m$—$NR^{14}R^{15}$;
$R^{10}$ is hydrogen or $C_{1-7}$-alkyl;
$R^{11}$ is hydrogen or $C_{1-7}$-alkyl;
$R^{12}$ is hydrogen or $C_{1-7}$-alkyl;
$R^{13}$ is hydrogen or $C_{1-7}$-alkyl;
$R^{14}$ and $R^{15}$ are independently selected from hydrogen, $C_{1-7}$-alkyl and $C_{3-8}$-cycloalkyl;
n is 0, 1 or 2;
m is 0, 1, 2 or 3;
or $R^9$ and $R^{10}$ together form $C_{1-7}$-alkylene;
or $R^9$ and $R^{12}$ together form $C_{1-7}$-alkylene;
or $R^{10}$ and $R^{11}$ together form $C_{2-7}$-alkylene;
or $R^{10}$ and $R^{12}$ together form $C_{1-7}$-alkylene;
or $R^{10}$ and $R^{14}$ together form $C_{1-7}$-alkylene;
or $R^{12}$ and $R^{13}$ together form $C_{2-7}$-alkylene;
or $R^{12}$ and $R^{14}$ together form $C_{1-7}$-alkylene;
or $R^{14}$ and $R^{15}$ together form $C_{2-7}$-alkylene which is optionally substituted with alkoxy;

with the proviso that if Z is CH then $R^9$ is —$(CH_2)_m$—$NR^{14}R^{15}$; and
with the proviso that if Z is N and $R^9$ is —$(CH_2)_m$—$NR^{14}R^{15}$ then m is 2 or 3.

A particular embodiment of the present invention relates to compounds of formula (I), wherein A is

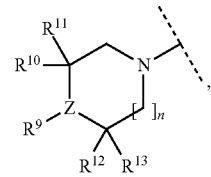

wherein Y, n, $R^9$, $R^{10}$, $R^{11}$, $R^{12}$ and $R^{13}$ are as defined above.

It has been found that brain penetration is improved when at least one of $R^9$, $R^{10}$, $R^{11}$, $R^{12}$ and $R^{13}$ is not hydrogen. In a particular embodiment of the invention at least one of $R^9$, $R^{10}$, $R^{11}$, $R^{12}$ and $R^{13}$ is other than hydrogen.

A particular embodiment of the present invention relates to compounds of formula (I), wherein Z is N.

A particular embodiment of the present invention relates to compounds of formula (I), wherein Z is CH and $R^9$ is —$(CH_2)_m$—$NR^{14}R^{15}$.

A particular embodiment of the present invention relates to compounds of formula (I), wherein Z is CH, $R^9$ is —$(CH_2)_m$—$N(CH_3)_2$, and m is 0.

A particular embodiment of the present invention relates to compounds of formula (I), wherein n is 1.

A particular embodiment of the present invention relates to compounds of formula (I), wherein $R^9$ is hydrogen, $C_{1-7}$-alkyl, amino, heterocycloalkyl, and heterocycloalkyl-$C_{1-7}$-alkyl.

A particular embodiment of the present invention relates to compounds of formula (I), wherein $R^9$ is hydrogen, methyl, ethyl, —$N(CH_3)_2$, azetidinyl, oxetanyl, or —$CH_2$-pyrrolidinyl.

A particular embodiment of the present invention relates to compounds of formula (I), wherein $R^9$ is hydrogen ethyl or methyl.

A particular embodiment of the present invention relates to compounds of formula (I), wherein $R^{10}$ is hydrogen or $C_{1-7}$-alkyl.

A particular embodiment of the present invention relates to compounds of formula (I), wherein $R^{10}$ is hydrogen, methyl, ethyl or isopropyl, more particularly methyl.

A particular embodiment of the present invention relates to compounds of formula (I), wherein $R^{11}$ is hydrogen or methyl, more particularly hydrogen.

A particular embodiment of the present invention relates to compounds of formula (I), wherein $R^{12}$ is hydrogen or methyl, more particularly hydrogen.

A particular embodiment of the present invention relates to compounds of formula (I), wherein $R^{13}$ is hydrogen.

A particular embodiment of the present invention relates to compounds of formula (I), wherein $R^9$ and $R^{10}$ together form propylene.

A particular embodiment of the present invention relates to compounds of formula (I), wherein $R^{10}$ and $R^{11}$ together form ethylene.

A particular embodiment of the present invention relates to compounds of formula (I), wherein $R^{14}$ and $R^{15}$ together form propylene or butylene.

A particular embodiment of the present invention relates to compounds of formula (I), wherein $R^{14}$ and $R^{15}$ together form propylene.

A particular embodiment of the present invention relates to compounds of formula (I), wherein $R^{14}$ and $R^{15}$ together form butylene.

A particular embodiment of the present invention relates to compounds of formula (I), wherein A is $NR^5R^6$, wherein $R^5$ and $R^6$ are as described herein.

A particular embodiment of the present invention relates to compounds of formula (I), wherein A is selected from the group of:

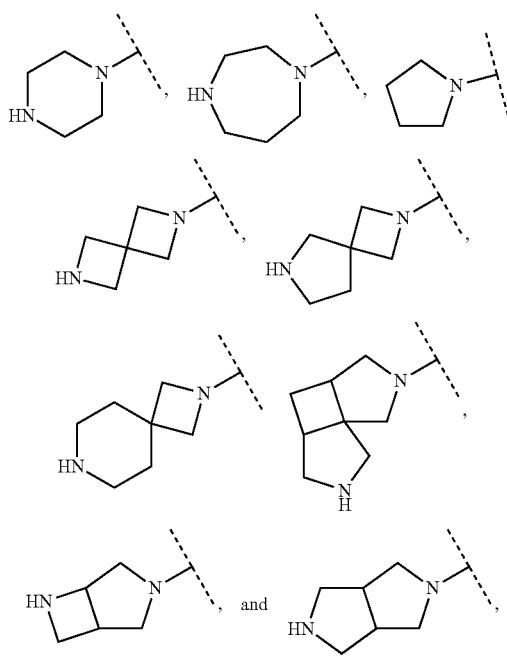

and wherein A is optionally substituted with 1 or 2 substituents selected from $R^7$ as described herein.

A particular embodiment of the present invention relates to compounds of formula (I), wherein A is selected from the group of:

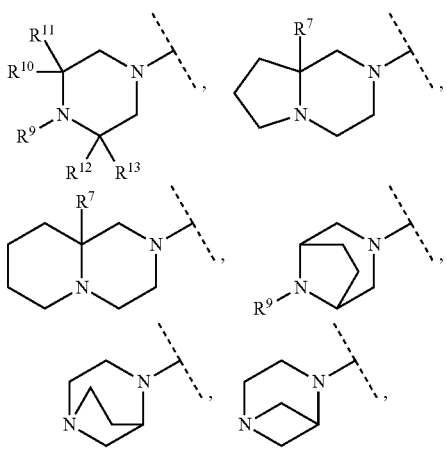

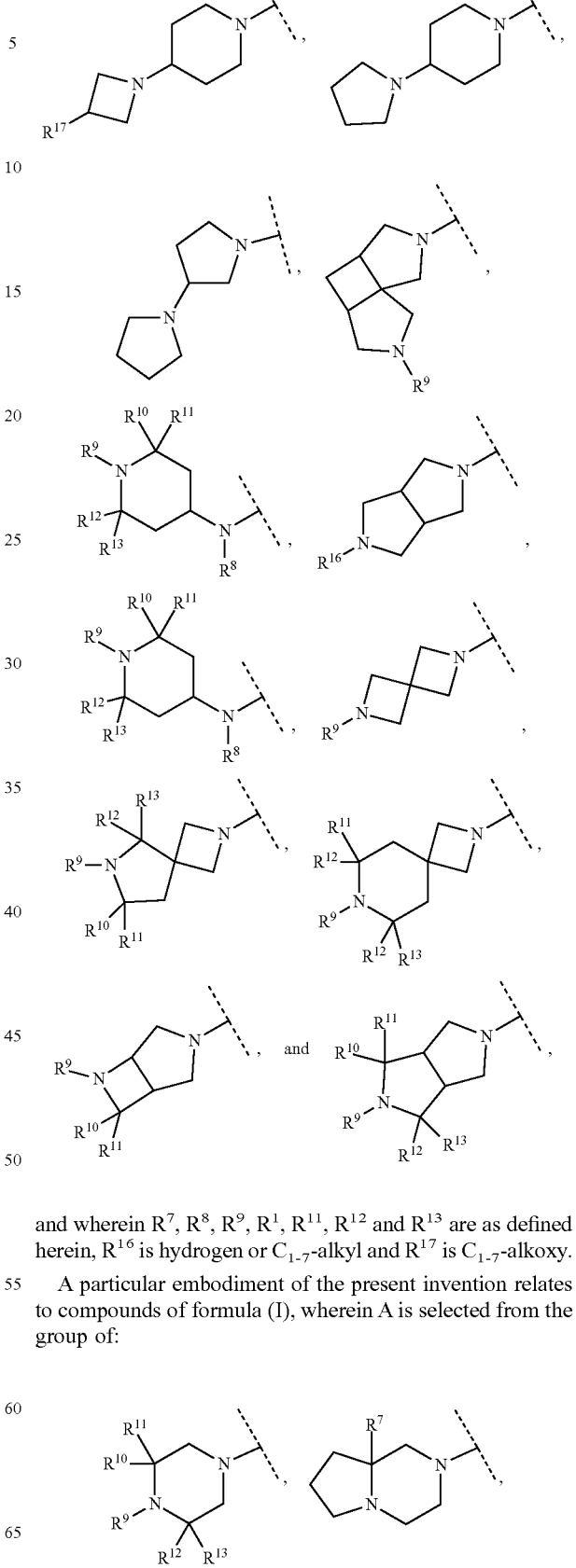

and wherein $R^7$, $R^8$, $R^9$, $R^1$, $R^{11}$, $R^{12}$ and $R^{13}$ are as defined herein, $R^{16}$ is hydrogen or $C_{1-7}$-alkyl and $R^{17}$ is $C_{1-7}$-alkoxy.

A particular embodiment of the present invention relates to compounds of formula (I), wherein A is selected from the group of:

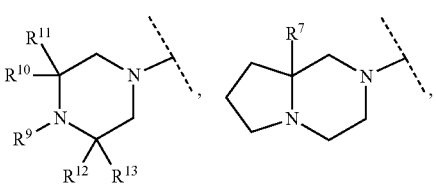

-continued

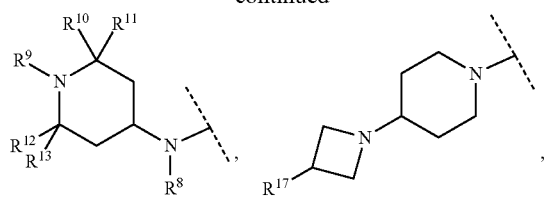

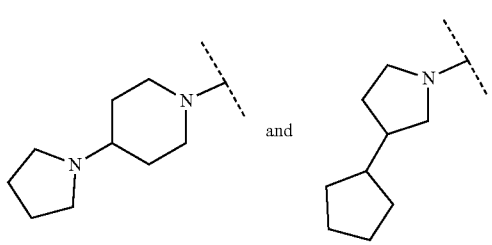

wherein $R^7$, $R^8$, $R^9$, $R^{10}$, $R^{11}$, $R^{12}$, and $R^{13}$ are as defined herein and $R^{17}$ is $C_{1-7}$-alkoxy.

A particular embodiment of the present invention relates to compounds of formula (I), wherein A is selected from the group of pyrrolidinyl, piperidyl, piperazinyl, 1,4-diazepanyl, 2,6-diazaspiro[3.3]heptanyl, 2,7-diazaspiro[3.4]octanyl, 2,7-diazaspiro[3.5]nonanyl, 3,6-diazabicyclo[3.2.0]heptanyl, 1,3,3a,4,6,6a-hexahydropyrrolo[3,4-c]pyrrolyl, and hexahydro-1H-cyclobuta[1,2-c:1,4-c']dipyrrol-2(3H)-yl, each optionally substituted with 1 or 2 substituents selected from $R^7$ as defined herein.

A particular embodiment of the present invention relates to compounds of formula (I), wherein A is selected from the group of pyrrolidin-1-yl, 1-piperidyl, piperazin-1-yl, 1,4-diazepan-1-yl, 2,6-diazaspiro[3.3]heptan-2-yl, 2,7-diazaspiro[3.4]octan-2-yl, 2,7-diazaspiro[3.5]nonan-2-yl, 3,6-diazabicyclo[3.2.0]heptan-3-yl, 1,3,3a,4,6,6a-hexahydropyrrolo[3,4-c]pyrrol-5-yl, and hexahydro-1H-cyclobuta[1,2-c:1,4-c']dipyrrol-2(3H)-yl, each optionally substituted with 1 or 2 substituents selected from $R^7$ as defined herein.

A particular embodiment of the present invention relates to compounds of formula (I), wherein A is selected from the group of pyrrolidin-1-yl, piperazin-1-yl, 2,6-diazaspiro[3.3]heptan-2-yl, 2,7-diazaspiro[3.5]nonan-2-yl, 1,3,3a,4,6,6a-hexahydropyrrolo[3,4-c]pyrrol-5-yl, and hexahydro-1H-cyclobuta[1,2-c:1,4-c']dipyrrol-2(3H)-yl, each optionally substituted with 1 or 2 substituents selected from $R^7$ as defined herein.

A particular embodiment of the present invention relates to compounds of formula (I), wherein A is

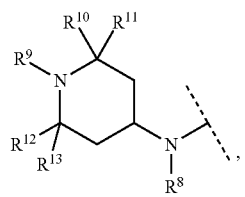

wherein $R^8$, $R^9$, $R^{10}$, $R^{11}$, $R^{12}$ and $R^{13}$ are as described herein.

A particular embodiment of the present invention relates to compounds of formula (I), wherein A is

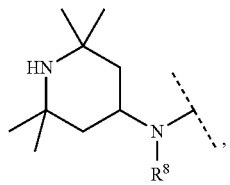

wherein $R^8$ is hydrogen or methyl.

A particular embodiment of the present invention relates to compounds of formula (I), wherein A is selected from the group of:

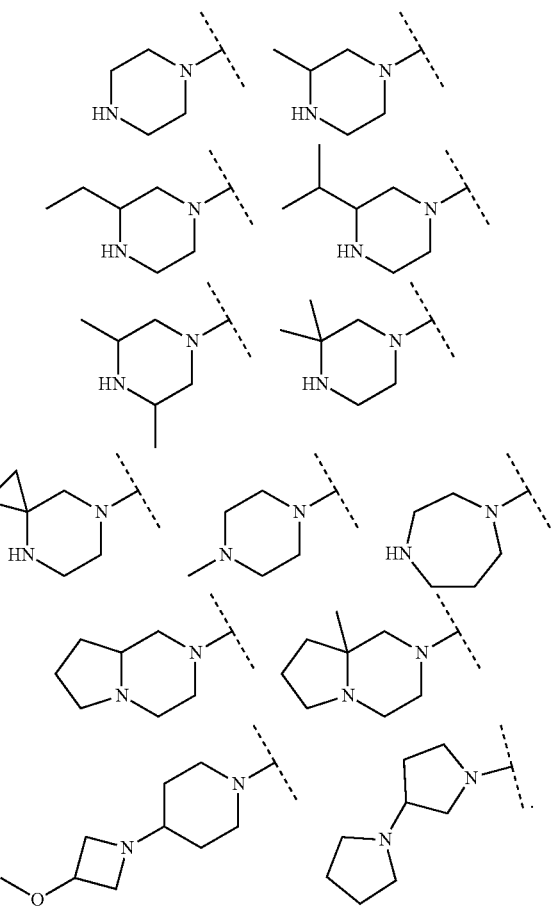

A particular embodiment of the present invention relates to compounds of formula (I), wherein A is selected from the group of:

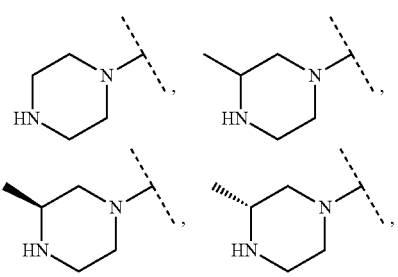

-continued
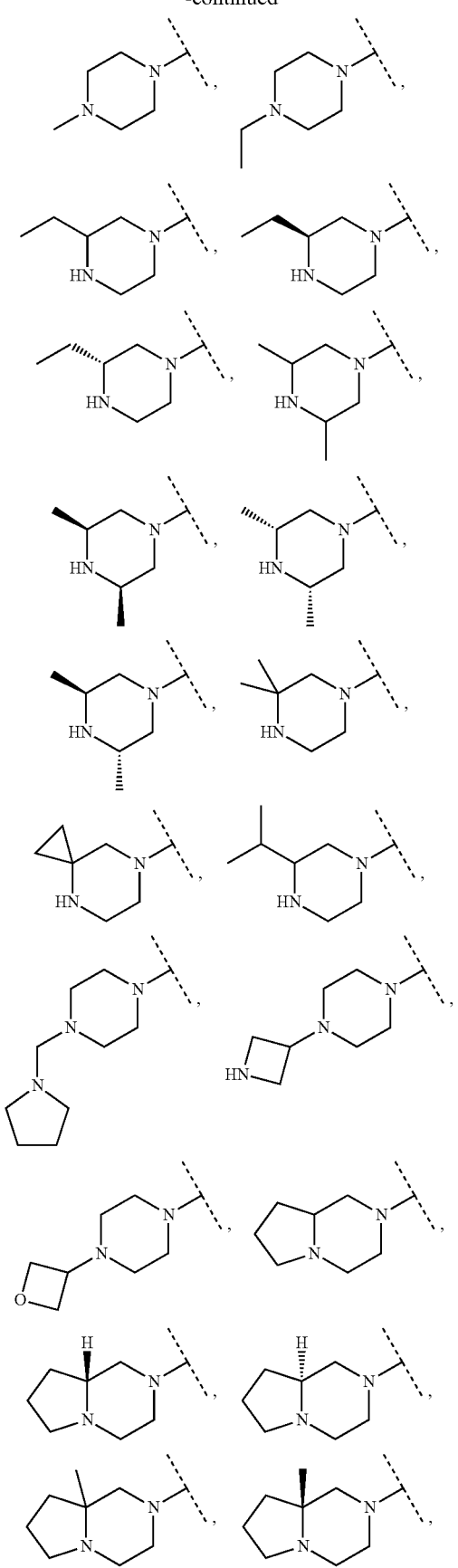
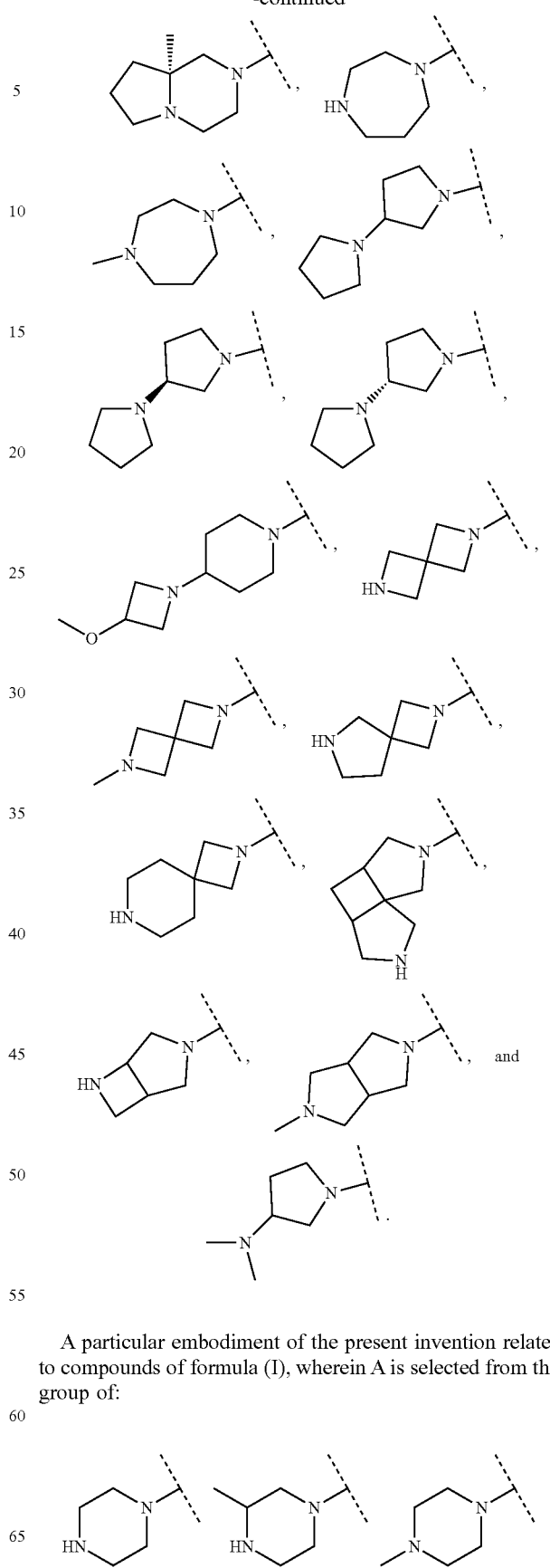
A particular embodiment of the present invention relates to compounds of formula (I), wherein A is selected from the group of:

-continued

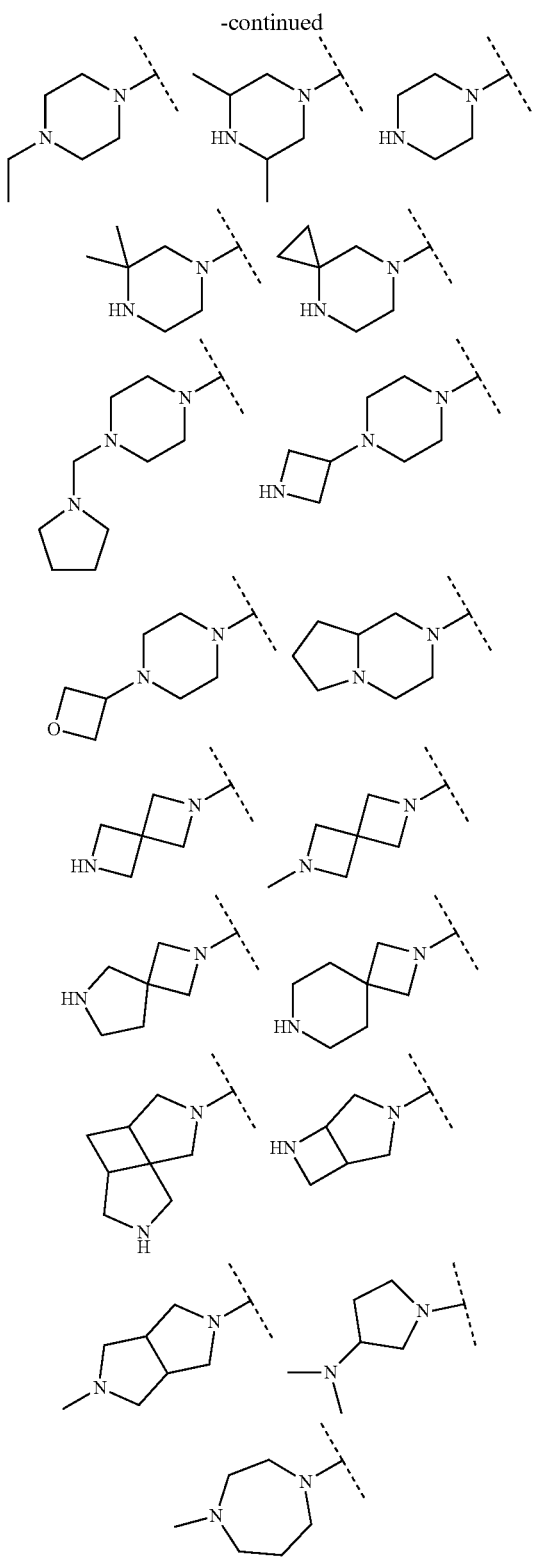

Particular compounds of formula (I) of the present invention are those selected from the group consisting of:
2-(2-methyl-[1,2,4]triazolo[1,5-a]pyrimidin-6-yl)-7-piperazin-1-yl-pyrido[1,2-a]pyrimidin-4-one;
7-[(3R,5S)-3,5-dimethylpiperazin-1-yl]-2-(2-methyl-[1,2,4] triazolo[1,5-a]pyrimidin-6-yl)pyrido[1,2-a]pyrimidin-4-one;
7-[(3R)-3-(dimethylamino)pyrrolidin-1-yl]-2-(2-methyl-[1,2,4]triazolo[1,5-a]pyrimidin-6-yl)pyrido[1,2-a]pyrimidin-4-one;
7-(4-methyl-1,4-diazepan-1-yl)-2-(2-methyl-[1,2,4]triazolo[1,5-a]pyrimidin-6-yl)pyrido[1,2-a]pyrimidin-4-one;
7-(2,7-diazaspiro[3.5]nonan-2-yl)-2-(2-methyl-[1,2,4]triazolo[1,5-a]pyrimidin-6-yl)pyrido[1,2-a]pyrimidin-4-one;
7-(3,3-dimethylpiperazin-1-yl)-2-(2-methyl-[1,2,4]triazolo[1,5-a]pyrimidin-6-yl)pyrido[1,2-a]pyrimidin-4-one;
7-(2,6-diazaspiro[3.3]heptan-2-yl)-2-(2-methyl-[1,2,4]triazolo[1,5-a]pyrimidin-6-yl)pyrido[1,2-a]pyrimidin-4-one;
2-(2,8-7-(2-methyl-1,3,3a,4,6,6a-hexahydropyrrolo[3,4-c]pyrrol-5-yl)-2-(2-methyl-[1,2,4]triazolo[1,5-a]pyrimidin-6-yl)pyrido[1,2-a]pyrimidin-4-one;
7-(3,6-diazabicyclo[3.2.0]heptan-3-yl)-2-(2-methyl-[1,2,4] triazolo[1,5-a]pyrimidin-6-yl)pyrido[1,2-a]pyrimidin-4-one;
7-[4-(azetidin-3-yl)piperazin-1-yl]-2-(2-methyl-[1,2,4]triazolo[1,5-a]pyrimidin-6-yl)pyrido[1,2-a]pyrimidin-4-one;
7-[(3S,5S)-3,5-dimethylpiperazin-1-yl]-2-(2-methyl-[1,2,4] triazolo[1,5-a]pyrimidin-6-yl)pyrido[1,2-a]pyrimidin-4-one;
2-(2-methyl-[1,2,4]triazolo[1,5-a]pyrimidin-6-yl)-7-[4-(pyrrolidin-1-ylmethyl)-1-piperidyl]pyrido[1,2-a]pyrimidin-4-one;
7-(4,7-diazaspiro[2.5]octan-7-yl)-2-(2-methyl-[1,2,4]triazolo[1,5-a]pyrimidin-6-yl)pyrido[1,2-a]pyrimidin-4-one;
2-(2-methyl-[1,2,4]triazolo[1,5-a]pyrimidin-6-yl)-7-[4-(oxetan-3-yl)piperazin-1-yl]pyrido[1,2-a]pyrimidin-4-one;
9-methyl-2-(2-methyl-[1,2,4]triazolo[1,5-b]pyridazin-6-yl)-7-piperazin-1-yl-pyrido[1,2-a]pyrimidin-4-one;
7-[(3S)-3-methylpiperazin-1-yl]-2-(2-methyl-[1,2,4]triazolo[1,5-a]pyrimidin-6-yl)pyrido[1,2-a]pyrimidin-4-one;
7-[(3R)-3-methylpiperazin-1-yl]-2-(2-methyl-[1,2,4]triazolo[1,5-b]pyridazin-6-yl)pyrido[1,2-a]pyrimidin-4-one;
7-[(3S)-3-methylpiperazin-1-yl]-2-(2-methyl-[1,2,4]triazolo[1,5-b]pyridazin-6-yl)pyrido[1,2-a]pyrimidin-4-one;
2-(2-methyl-[1,2,4]triazolo[1,5-b]pyridazin-6-yl)-7-piperazin-1-yl-pyrido[1,2-a]pyrimidin-4-one;
7-(4-methyl-1,4-diazepan-1-yl)-2-(2-methyl-[1,2,4]triazolo[1,5-b]pyridazin-6-yl)pyrido[1,2-a]pyrimidin-4-one;
7-(6-methyl-2,6-diazaspiro[3.3]heptan-2-yl)-2-(2-methyl-[1,2,4]triazolo[1,5-a]pyrimidin-6-yl)pyrido[1,2-a]pyrimidin-4-one;
7-[(3R,5S)-3,5-dimethylpiperazin-1-yl]-2-(2-methyl-[1,2,4] triazolo[1,5-b]pyridazin-6-yl)pyrido[1,2-a]pyrimidin-4-one;
7-(4-methylpiperazin-1-yl)-2-(2-methyl-[1,2,4]triazolo[1,5-a]pyrimidin-6-yl)pyrido[1,2-a]pyrimidin-4-one;
7-[(3R)-3-methylpiperazin-1-yl]-2-(2-methyl-[1,2,4]triazolo[1,5-a]pyrimidin-6-yl)pyrido[1,2-a]pyrimidin-4-one;
9-methyl-7-(4-methyl-1,4-diazepan-1-yl)-2-(2-methyl-[1,2,4]triazolo[1,5-b]pyridazin-6-yl)pyrido[1,2-a]pyrimidin-4-one;
7-[(3R,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;
9-methyl-7-(4-methylpiperazin-1-yl)-2-(2-methyl-[1,2,4]triazolo[1,5-b]pyridazin-6-yl)pyrido[1,2-a]pyrimidin-4-one;

7-(3,3-dimethylpiperazin-1-yl)-9-methyl-2-(2-methyl-[1,2,4]triazolo[1,5-b]pyridazin-6-yl)pyrido[1,2-a]pyrimidin-4-one;

7-[(3aS,6aR)-2-methyl-1,3,3a,4,6,6a-hexahydropyrrolo[3,4-c]pyrrol-5-yl]-9-methyl-2-(2-methyl-[1,2,4]triazolo[1,5-b]pyridazin-6-yl)pyrido[1,2-a]pyrimidin-4-one;

7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one;

9-methyl-2-(2-methyl-[1,2,4]triazolo[1,5-b]pyridazin-6-yl)-7-[4-(oxetan-3-yl)piperazin-1-yl]pyrido[1,2-a]pyrimidin-4-one;

7-(4-ethylpiperazin-1-yl)-9-methyl-2-(2-methyl-[1,2,4]triazolo[1,5-b]pyridazin-6-yl)pyrido[1,2-a]pyrimidin-4-one;

7-(2-methyl-1,3,3a,4,6,6a-hexahydropyrrolo[3,4-c]pyrrol-5-yl)-2-(2-methyl-[1,2,4]triazolo[1,5-b]pyridazin-6-yl)pyrido[1,2-a]pyrimidin-4-one;

7-[(8aR)-3,4,6,7,8,8a-hexahydro-1H-pyrrolo[1,2-a]pyrazin-2-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one;

7-[(8aR)-3,4,6,7,8,8a-hexahydro-1H-pyrrolo[1,2-a]pyrazin-2-yl]-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-2-(2-methyl-[1,2,4]triazolo[1,5-b]pyridazin-6-yl)pyrido[1,2-a]pyrimidin-4-one;

7-(4-methylpiperazin-1-yl)-2-(2-methyl-[1,2,4]triazolo[1,5-b]pyridazin-6-yl)pyrido[1,2-a]pyrimidin-4-one;

9-methyl-7-[(3R)-3-methylpiperazin-1-yl]-2-(2-methyl-[1,2,4]triazolo[1,5-b]pyridazin-6-yl)pyrido[1,2-a]pyrimidin-4-one;

7-[(3R)-3-(dimethylamino)pyrrolidin-1-yl]-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-2-(2-methyl-[1,2,4]triazolo[15-b]pyridazin-6-yl)pyrido[1,2-a]pyrimidin-4-one;

7-(4-ethylpiperazin-1-yl)-2-(2-methyl-[1,2,4]triazolo[1,5-b]pyridazin-6-yl)pyrido[1,2-a]pyrimidin-4-one;

7-(4,7-diazaspiro[2.5]octan-7-yl)-2-(2-methyl-[1,2,4]triazolo[1,5-b]pyridazin-6-yl)pyrido[1,2-a]pyrimidin-4-one;

9-methyl-7-[(3S)-3-methylpiperazin-1-yl]-2-(2-methyl-[1,2,4]triazolo[1,5-b]pyridazin-6-yl)pyrido[1,2-a]pyrimidin-4-one;

7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one;

7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one;

7-(2,7-diazaspiro[3.4]octan-2-yl)-9-methyl-2-(2-methyl-[1,2,4]triazolo[5-b]pyridazin-6-yl)pyrido[1,2-a]pyrimidin-4-one;

and pharmaceutically acceptable salts thereof.

Particular compounds of formula (I) of the present invention are those selected from the group consisting of:

7-(2,7-diazaspiro[3.5]nonan-2-yl)-2-(2-methyl-[1,2,4]triazolo[1,5-b]pyridazin-6-yl)pyrido[1,2-a]pyrimidin-4-one;

2-(2-methyl-[1,2,4]triazolo[1,5-b]pyridazin-6-yl)-7-piperazin-1-yl-pyrido[1,2-a]pyrimidin-4-one;

7-(3,3-dimethylpiperazin-1-yl)-9-methyl-2-(2-methyl-[1,2,4]triazolo[1,5-b]pyridazin-6-yl)pyrido[1,2-a]pyrimidin-4-one;

7-[(3aS,6aR)-2-methyl-1,3,3a,4,6,6a-hexahydropyrrolo[3,4-c]pyrrol-5-yl]-9-methyl-2-(2-methyl-[1,2,4]triazolo[1,5-b]pyridazin-6-yl)pyrido[1,2-a]pyrimidin-4-one;

7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one;

7-(4-ethylpiperazin-1-yl)-9-methyl-2-(2-methyl-[1,2,4]triazolo[1,5-b]pyridazin-6-yl)pyrido[1,2-a]pyrimidin-4-one;

7-(2-methyl-1,3,3a,4,6,6a-hexahydropyrrolo[3,4-c]pyrrol-5-yl)-2-(2-methyl-[1,2,4]triazolo[1,5-b]pyridazin-6-yl)pyrido[1,2-a]pyrimidin-4-one;

7-[(8aR)-3,4,6,7,8,8a-hexahydro-1H-pyrrolo[1,2-a]pyrazin-2-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-2-(2-methyl-[1,2,4]triazolo[1,5-b]pyridazin-6-yl)pyrido[1,2-a]pyrimidin-4-one;2,2,2-trifluoroacetic acid;

9-methyl-7-[(3R)-3-methylpiperazin-1-yl]-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-2-(2-methyl-[1,2,4]triazolo[1,5-b]pyridazin-6-yl)pyrido[1,2-a]pyrimidin-4-one;

7-(4-ethylpiperazin-1-yl)-2-(2-methyl-[1,2,4]triazolo[1,5-b]pyridazin-6-yl)pyrido[1,2-a]pyrimidin-4-one;

7-(4,7-diazaspiro[2.5]octan-7-yl)-2-(2-methyl-[1,2,4]triazolo[1,5-b]pyridazin-6-yl)pyrido[1,2-a]pyrimidin-4-one;

9-methyl-7-[(3S)-3-methylpiperazin-1-yl]-2-(2-methyl-[1,2,4]triazolo[1,5-b]pyridazin-6-yl)pyrido[1,2-a]pyrimidin-4-one;

7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one;

7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one;

and pharmaceutically acceptable salts thereof.

Compounds of formula (VI) are suitable as intermediates in the manufacture of compounds of formula (I).

Another embodiment of the invention relates to compounds of formula (VI)

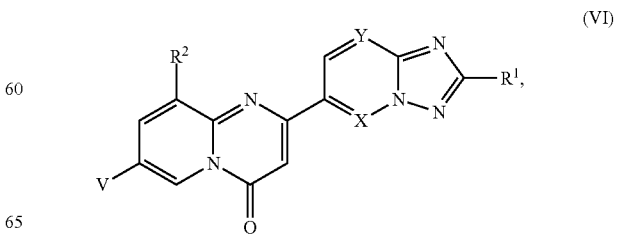

wherein X, Y, R¹ and R² are as described herein;

V is halogen or trifluoromethanesulfonate;

or salts thereof.

A particular embodiment of the present invention relates to compounds of formula (VI), wherein V is fluoro, chloro, bromo, iodo or trifluoromethanesulfonate, particularly fluoro or bromo, most particularly fluoro.

Particular compounds of formula (VI) of the present invention are those selected from the group consisting of:

7-fluoro-2-(2-methyl-[1,2,4]triazolo[1,5-a]pyrimidin-6-yl) pyrido[1,2-a]pyrimidin-4-one;

7-fluoro-2-(2-methyl-[1,2,4]triazolo[1,5-b]pyridazin-6-yl) pyrido[1,2-a]pyrimidin-4-one;

7-fluoro-9-methyl-2-(2-methyl-[1,2,4]triazolo[1,5-b] pyridazin-6-yl)pyrido[1,2-a]pyrimidin-4-one; and salts thereof.

Manufacturing Processes

Compounds of formula (I) or pharmaceutically acceptable salts thereof as defined above can be prepared following standard methods known in the art. In particular, compound of formula (I) can be prepared according to Scheme 1.

Scheme 1. General preparation of compounds of formula (I).

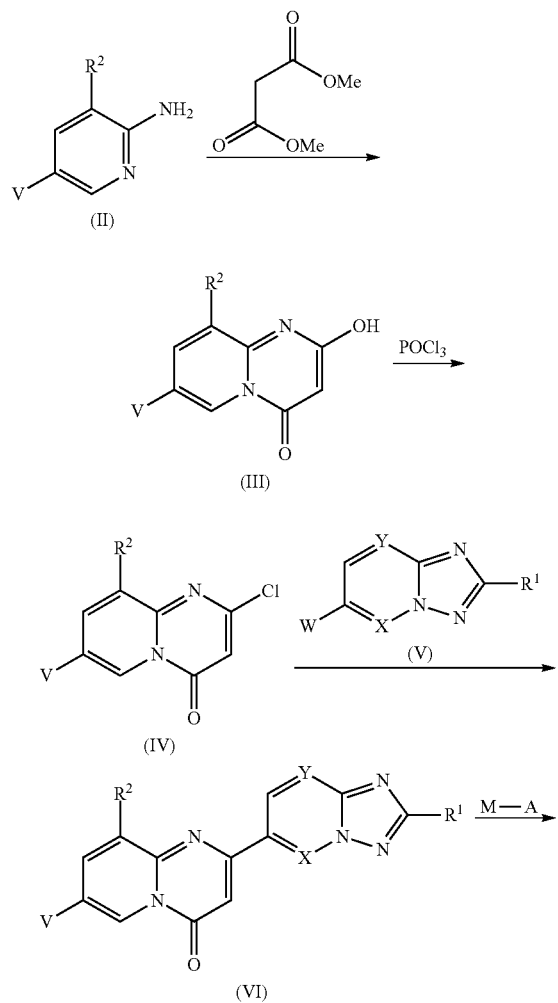

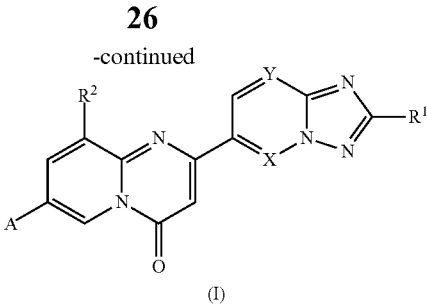

The commercially available amino-pyridine of formula (II) is reacted with malonic ester to afford the compound of formula (III), wherein V is halogen or trifluoromethanesulfonate and R² is as defined herein. Compound (III) is then treated with a chlorinating reagent (such as POCl₃ and the like) to provide the compound of formula (IV). Compound (IV) undergoes a Suzuki cross-coupling reaction with a compound of formula (V) in the presence of a catalyst (such as Pd(dppf)Cl₂ and the like) and a base (such as K₂CO₃ and the like) in a suitable solvent (such as DMF and the like), to afford the compound of formula (VI), wherein W is B(OH)₂ or an alkyl pinacolic boronic acid ester and X, Y and R¹ are as defined herein. Finally, the compound of formula (VI) undergoes a reaction with an amine moiety of formula M-A to give the final compound of formula (I), wherein A is as defined herein, M is hydrogen, sodium or potassium, particularly hydrogen, and wherein M is linked to A via a nitrogen atom of A.

In more detail, the compound of formula (VI) is reacted with a compound M-A either in:

a) an aromatic nucleophilic substitution reaction (particularly if V is fluoro) by heating at a temperature from 80° C. to 200° C. in a solvent (e.g. dimethyl sulfoxide (DMSO), N-methylpyrrolidone (NMP), or dimethylformamide (DMF)); or b) a Buchwald-Hartwig amination reaction (particularly if V is bromo) in the presence of a catalyst (e.g. tris (dibenzylidene-acetone)dipalladium(0) (Pd₂(dba)₃)) a ligand (e.g. 2,2'-bis(diphenylphosphino)-1,1'-binaphthyl), a base (e.g. cesium carbonate) by heating at a temperature from 20° C. to 100° C. in a solvent (e.g. toluene);

to give a compound of formula (I), wherein A is as defined herein, M is hydrogen, sodium or potassium, particularly hydrogen, and wherein M is linked to A via a nitrogen atom of A.

In one embodiment, the invention relates to a process for the manufacture of compounds of formula (I) or pharmaceutically acceptable salts thereof as defined above, comprising the reaction of a compound of formula (VI) with a compound M-A either in:

a) an aromatic nucleophilic substitution reaction (particularly if V is fluoro) by heating at a temperature from 80° C. to 200° C. in a solvent (particularly dimethyl sulfoxide (DMSO), N-methylpyrrolidone (NMP), or dimethylformamide (DMF)); or b) a Buchwald-Hartwig amination reaction (particularly if V is bromo) in the presence of a catalyst (particularly tris(dibenzylidene-acetone)dipalladium(0) (Pd₂ (dba)₃)) a ligand (particularly 2,2'-bis(diphenylphosphino)-1,1'-binaphthyl), a base (particularly cesium carbonate) by heating at a temperature from 20° C. to 100° C. in a solvent (particularly toluene);

wherein A, V, X, Y, R¹ and R² are as defined herein, M is hydrogen, sodium or potassium, particularly hydrogen, and wherein M is linked to A via a nitrogen atom of A.

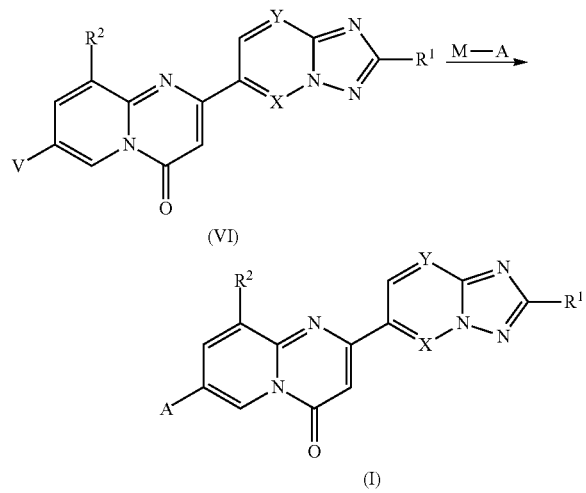

Particularly, compounds of formula (I) or pharmaceutically acceptable salts thereof can be prepared in accordance to the methods described in the examples herein.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 m filter, to remove impurities and contaminants.

Uses

As described above, the compounds of formula (I) and their pharmaceutically acceptable salts possess valuable pharmacological properties and have been found to enhance inclusion of exon 7 of SMN1 and/or SMN2 into mRNA transcribed from the SMN1 and/or SMN2 gene, thereby increasing expression of SMN protein in a human subject in need thereof.

The compounds of the present invention can be used, either alone or in combination with other drugs, for the treatment or prevention of diseases caused by an inactivating mutation or deletion in the SMN1 gene and/or associated with loss or defect of SMN1 gene function. These diseases include, but are not limited to spinal muscular atrophy (SMA).

A particular embodiment of the present invention relates to pharmaceutical compositions comprising compounds of formula (I) as defined above or their pharmaceutically acceptable salts as defined above and one or more pharmaceutically acceptable excipients.

A particular embodiment of the present invention relates to pharmaceutical compositions comprising compounds of formula (I) or their pharmaceutically acceptable salts as defined above and one or more pharmaceutically acceptable excipients for the treatment or prevention of diseases caused by an inactivating mutation or deletion in the SMN1 gene and/or associated with loss or defect of SMN1 gene function, particularly for the treatment or prevention of SMA.

A particular embodiment of the present invention relates to compounds of formula (I) or their pharmaceutically acceptable salts as defined above for use as therapeutically active substances, particularly for use in the treatment or prevention of a SMN-deficiency-related condition, more particularly for use in the treatment or prevention of diseases caused by an inactivating mutation or deletion in the SMN1 gene and/or associated with loss or defect of SMN1 gene function, most particularly for use in the treatment or prevention of spinal muscular atrophy (SMA).

A particular embodiment of the present invention relates to compounds of formula (I) or their pharmaceutically acceptable salts as defined above for use in the treatment or prevention of a SMN-deficiency-related condition, particularly for use in the treatment or prevention of diseases caused by an inactivating mutation or deletion in the SMN1 gene and/or associated with loss or defect of SMN1 gene function, more particularly for use in the treatment or prevention of spinal muscular atrophy (SMA).

A particular embodiment of the present invention relates to a method for the treatment or prevention of a SMN-deficiency-related condition, particularly to a method for the treatment or prevention of diseases caused by an inactivating mutation or deletion in the SMN1 gene and/or associated with loss or defect of SMN1 gene function, more particularly for the treatment or prevention of spinal muscular atrophy (SMA), which method comprises administering compounds of formula (I) or their pharmaceutically acceptable salts as defined above to a subject.

A particular embodiment of the present invention relates to the use of compounds of formula (I) or their pharmaceutically acceptable salts as defined above in the treatment or prevention of a SMN-deficiency-related condition, particularly for use in the treatment or prevention of diseases caused by an inactivating mutation or deletion in the SMN1 gene and/or associated with loss or defect of SMN1 gene function, more particularly for use in the treatment or prevention of spinal muscular atrophy (SMA).

A particular embodiment of the present invention relates to the use of compounds of formula (I) or their pharmaceutically acceptable salts as defined above for the preparation of medicaments for the treatment or prevention of diseases caused by an inactivating mutation or deletion in the SMN1 gene and/or associated with loss or defect of SMN1 gene function, particularly for the treatment or prevention of spinal muscular atrophy (SMA). Such medicaments comprise compounds of formula (I) or their pharmaceutically acceptable salts as defined above.

EXAMPLES

The invention will be more fully understood by reference to the following examples. They should however not be construed as limiting the scope of the invention.

Abbreviations Used

ACN: acetonitrile; AcOH: acetic acid; Boc: tert-butyloxycarbonyl; $B_2(pin)_2$: bis(pinacolato)diboron; CBZ: benzyloxycarbonyl; CDI: 1,1'-carbonyldiimidazole; DCM: dichloromethane ($CH_2Cl_2$); dba: dibenzylideneacetone; DIPEA: diisopropyl ethylamine; DMA: dimethyl acetamide; DMF: dimethylformamide; DMSO: dimethyl sulfoxide; dppf: 1,1'-bis(diphenylphosphino)ferrocene; EtOH: ethanol; MeOH: methanol; NMP: N-methylpyrrolidone; $Pd_2(dba)_3$: tris(dibenzylidene-acetone)dipalladium(0); $Pd(dppf)Cl_2$: (1,1'-bis(diphenylphosphino)ferrocene)palladium(II) dichloride;

PPTS: pyridinium p-toluenesulfonate; TEA: triethylamine; RT: room temperature; Xantphos: diphenylphosphino)-9,9-dimethylxanthene.

Intermediate (VI-1)

7-fluoro-2-(2-methyl-[1,2,4]triazolo[1,5-a]pyrimidin-6-yl)pyrido[1,2-a]pyrimidin-4-one

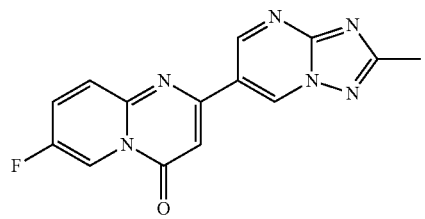 [SMILES: Cc1nc2ncc(-c3cc(=O)n4cc(F)ccc4n3)cn2n1]

Part 1: 2-chloro-7-fluoro-pyrido[1,2-a]pyrimidin-4-one

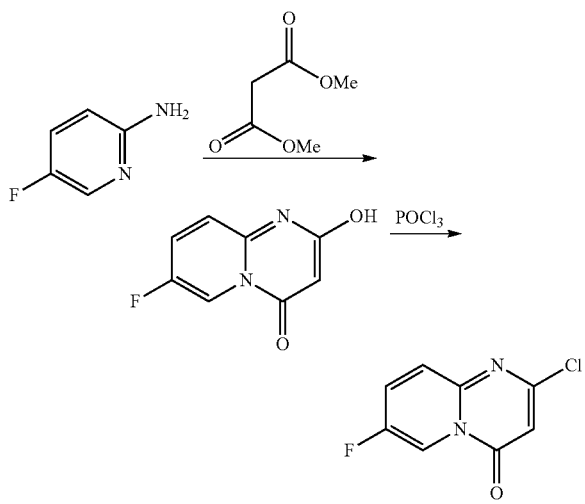

1a) 7-fluoro-2-hydroxy-pyrido[1,2-a]pyrimidin-4-one

A mixture of 2-amino-5-fluoropyridine (11.20 g, 0.10 mol) and dimethyl malonate (57.0 mL, 0.50 mol) was heated at 230° C. for 1.5 h. After cooling to room temperature, the precipitate was filtered and washed with ACN (3×) to give 7-fluoro-2-hydroxy-4H-pyrido[1,2-a]pyrimidin-4-one as a dark solid (14 g), which was used directly in the next step (m/z: 181.3 [M+H]$^+$).

1b) 2-chloro-7-fluoro-pyrido[1,2-a]pyrimidin-4-one

A dark mixture of crude 7-fluoro-2-hydroxy-4H-pyrido[1,2-a]pyrimidin-4-one (14 g, ~77 mmol) in $POCl_3$ (50 mL) and DIPEA (13.3 mL, 77 mmol) was heated at 110° C. for 15 h. The volatiles were removed and the dark residue was treated with ice-water, washed with water (3×) and dried to give a brown solid. The crude brown solid was purified by column chromatography ($SiO_2$, 5% MeOH in DCM) to give 2-chloro-7-fluoro-4H-pyrido[1,2-a]pyrimidin-4-one as a yellow solid (9.84 g, 50%, 2 steps, m/z: 199.2 [M+H]+).

Part 2: 2-methyl-6-(4,4,5,5-tetramethyl-1,3,2-dioxaborolan-2-yl)-[1,2,4]triazolo[1,5-a]pyrimidine

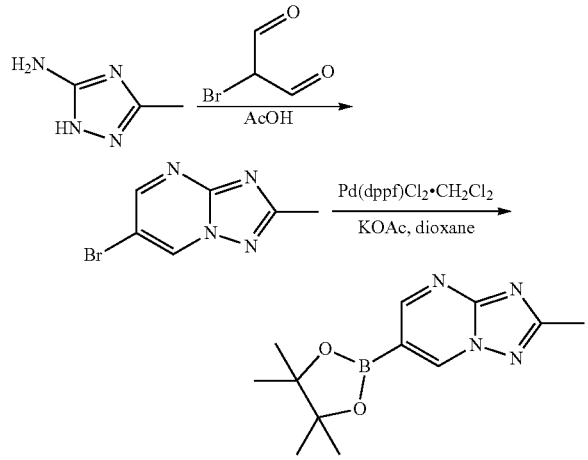

2a) 6-bromo-2-methyl-[1,2,4]triazolo[1,5-a]pyrimidine 3-methyl-1H-1,2,4-triazol-5-amine (4.7747 g, 48.7 mmol, 1 eq.) and 2-bromomalonaldehyde (8.08 g, 53.5 mmol, 1.1 eq.) were dissolved in AcOH (50 ml) and heated at 60° C. for 18 hours under inert conditions. The reaction mixture was concentrated under vacuo, then the crude material was redissolved in EtOAc and filtered. The filtrate was combined with NaHCO3, and the aqueous layer was extracted with EtOAc (×3). The combined organic extracts were dried over Na2SO4, filtered and concentrated in vacuo. The crude material was absorbed onto silica and purified by column chromatography (SiO2, 100% DCM, then 98:2 DCM:MeOH) to give 6-bromo-2-methyl-[1,2,4]triazolo[1,5-a]pyrimidine (2.22 g, 21%, m/z: 215.1 [M+H]+) as an off-white solid.

2b) 2-methyl-6-(4,4,5,5-tetramethyl-1,3,2-dioxaborolan-2-yl)-[1,2,4]triazolo[1,5-a]pyrimidine To a 25 mL round bottomed flask, 6-bromo-2-methyl-[1,2,4]triazolo[1,5-a]pyrimidine (100 mg, 0.469 mmol) and 4,4,4',4',5,5,5',5'-octamethyl-2,2'-bi(1,3,2-dioxaborolane) (119 mg, 0.469 mmol, 1 eq.) were stirred in 1,4-Dioxane (5 ml) under highly inert conditions. The reaction was degassed under vacuum and purged with argon (×3). PdCl2(dppf)-DCM adduct (57.5 mg, 0.070 mmol, 0.15 eq.) and potassium acetate (92.1 mg, 0.939 mmol, 2 eq.) were then added, and the reaction vessel was degassed and purged for a further three times. The reaction was heated under an inert atmosphere at 90° C. for 16 h. The volatiles were removed under vacuum and the crude product was directly used in the next step.

Part 3: 7-fluoro-2-(2-methyl-[1,2,4]triazolo[1,5-a]pyrimidin-6-yl)pyrido[1,2-a]pyrimidin-4-one

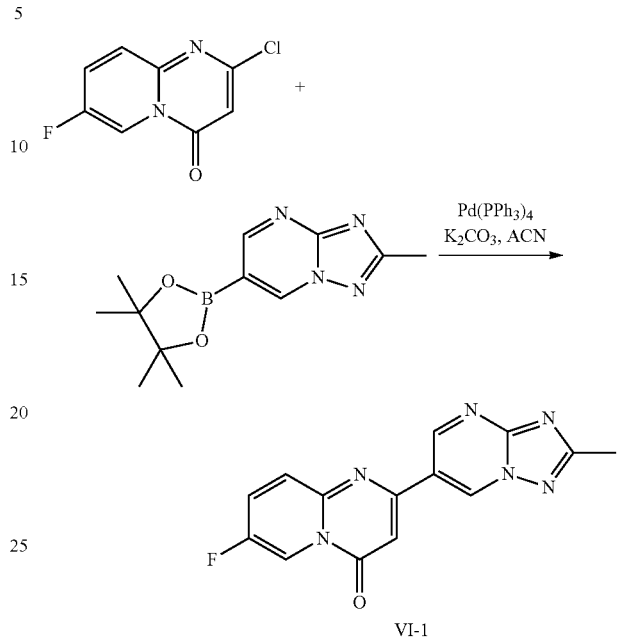

VI-1

To a round-bottomed flask containing 2-methyl-6-(4,4,5,5-tetramethyl-1,3,2-dioxaborolan-2-yl)-[1,2,4]triazolo[1,5-a]pyrimidine (2.73 g, 10.5 mmol), 2-chloro-7-fluoro-4H-pyrido[1,2-a]pyrimidin-4-one (2.08 g, 10.5 mmol, 1 eq.) and ACN (90 ml) were added. The reaction vessel was degassed and purged with argon three times. Tetrakis(triphenylphosphine)palladium (0) (1.21 g, 1.05 mmol, 0.1 eq.) and potassium carbonate (2.9 g, 21 mmol, 2 eq.) were then added, and the reaction vessel was degassed and purged a further three times. The reaction mixture was heated at 80° C. for 48 hours. The reaction mixture was concentrated in vacuo and the crude material was directly purified by column chromatography (SiO2, 3:1 EtOAc:Heptane, then DCM:MeOH 98:2-95:5). Trituration in EtOAc (×2) yielded 7-fluoro-2-(2-methyl-[1,2,4]triazolo[1,5-a]pyrimidin-6-yl)pyrido[1,2-a]pyrimidin-4-one (1.02 g, 33%, m/z=297 [M+H]+) as a yellow solid.

Pyridopyrimidinone Intermediate (VI-2)

7-fluoro-2-(2-methyl-[1,2,4]triazolo[1,5-b]pyridazin-6-yl)pyrido[1,2-a]pyrimidin-4-one

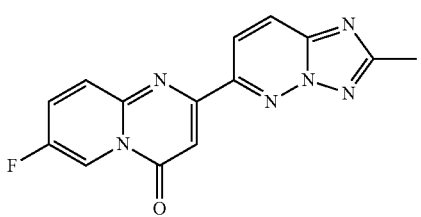 [SMILES: Cc1nc2ccc(-c3cc(=O)n4cc(F)ccc4n3)nn2n1]

Part 1: 2-methyl-6-(4,4,5,5-tetramethyl-1,3,2-dioxaborolan-2-yl)-[1,2,4]triazolo[1,5-b]pyridazine

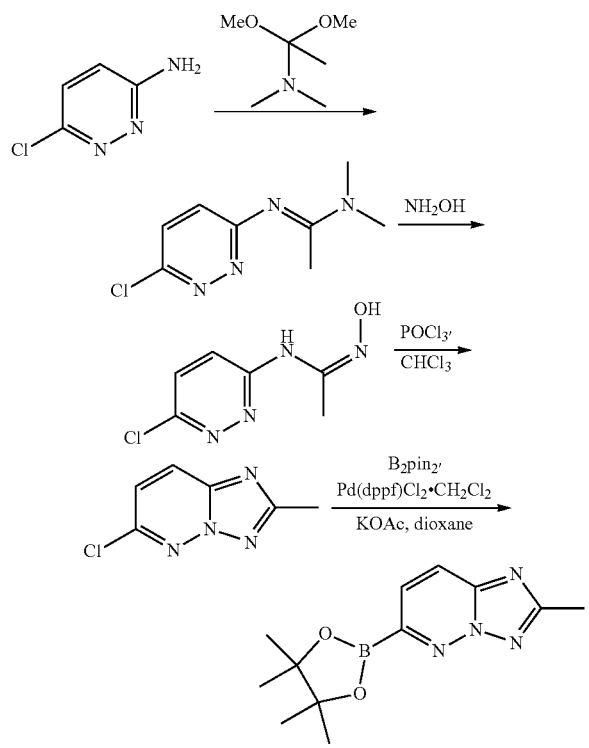

1a) N'-(6-chloropyridazin-3-yl)-N,N-dimethyl-acetamidine

A mixture of 6-chloropyridazin-3-amine (1.6 g, 12.4 mmol) and 1,1-dimethoxy-N,N-dimethylethanamine (1.97 g, 2.17 ml, 14.8 mmol, 1.2 eq.) in Toluene (15 ml) was refluxed under argon for 5 hours. The solvent was then removed in vacuo to obtain N'-(6-chloropyridazin-3-yl)-N,N-dimethyl-acetamidine, which was used directly in the next step (m/z: 199.1 [M+H]+).

1b) N-(6-chloropyridazin-3-yl)-N'-hydroxy-acetamidine

A mixture of N'-(6-chloropyridazin-3-yl)-N,N-dimethyl-acetamidine and hydroxylamine (490 mg, 405 μl, 14.8 mmol, 1.2 eq.) in MeOH (30 mL) and H$_2$O (7.5 mL) was heated at 85° C. for 6 hours and then stirred at ambient temperature over 2 days. The reaction mixture was concentrated in vacuo and purified by column chromatography (SiO$_2$, 95:5 DCM:MeOH) to yield N-(6-chloropyridazin-3-yl)-N'-hydroxy-acetamidine (827 mg, 36%, m/z: 187.1 [M+H]+) as an off white solid.

1c) 6-chloro-2-methyl-[1,2,4]triazolo[1,5-b]pyridazine

To a refluxing suspension of N-(6-chloropyridazin-3-yl)-N'-hydroxy-acetamidine (480 mg, 2.57 mmol, 1 eq.) in chloroform (32.8 ml), a solution of POCl$_3$ (2.96 g, 1.8 ml, 19.3 mmol, 7.5 eq.) in CHCl$_3$ (4 ml) was slowly added and the mixture was heated under reflux for 30 minutes. The reaction mixture was concentrated in vacuo to yield 6-chloro-2-methyl-[1,2,4]triazolo[1,5-b]pyridazine (413 mg, 2.45 mmol, 95.2% yield, m/z: 169.0 [M+H]+).

1d) 2-methyl-6-(4,4,5,5-tetramethyl-1,3,2-dioxaborolan-2-yl)-[1,2,4]triazolo[1,5-b]pyridazine To a 200 mL four-necked flask 6-chloro-2-methyl-[1,2,4]triazolo[1,5-b]pyridazine (0.85 g, 5.04 mmol), 4,4,4',4',5,5,5',5'-octamethyl-2,2'-bi(1,3,2-dioxaborolane) (1.28 g, 5.04 mmol, 1 eq.) and 1,4-Dioxane (53.6 ml) were stirred under highly inert conditions. The reaction vessel was degassed and purged with argon (×3). PdCl$_2$(dppf)-DCM adduct (553 mg, 756 mol, 0.15 eq.) and potassium acetate (990 mg, 10.1 mmol, 2 eq.) were then added, and the reaction mixture was degassed/purged a further three times. The reaction mixture was heated at 90° C. for 3.5 hours. The reaction mixture was then filtered through a decalite pad, concentrated in vacuo and used directly in the next step as a black oil.

Part 2: 7-fluoro-2-(2-methyl-[1,24]triazolo[1,5-b]pyridazin-6-yl)pyrido[12-a]pyrimidin-4-one

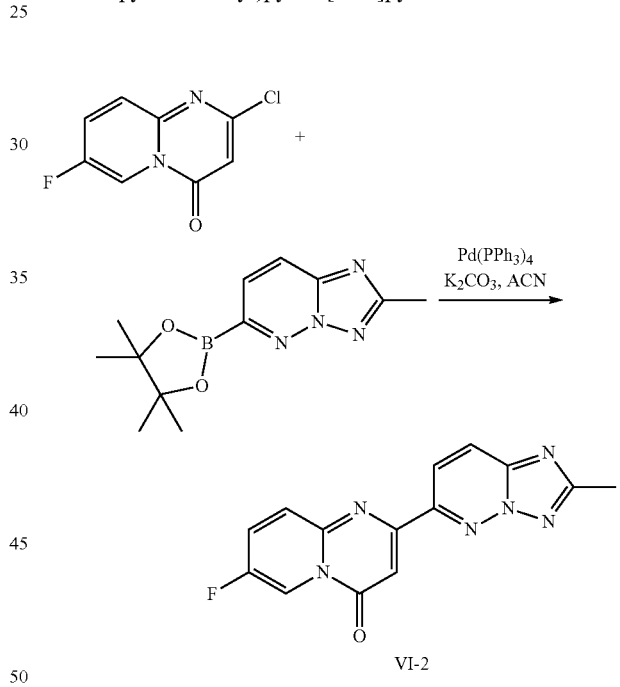

To a 100 mL four-necked flask, 2-methyl-6-(4,4,5,5-tetramethyl-1,3,2-dioxaborolan-2-yl)-[1,2,4]triazolo[1,5-b]pyridazine (1080 mg, 4.15 mmol), 2-chloro-7-fluoro-4H-pyrido[1,2-a]pyrimidin-4-one (989 mg, 4.98 mmol, 1.2 eq.), potassium carbonate (1.15 g, 8.3 mmol, 2 eq.) and ACN (35.5 ml) were added. The reaction vessel was degassed and purged with argon (×5). tetrakis(triphenylphosphine)palladium (0) (480 mg, 0.415 mmol, 0.1 eq.) was then added and the reaction vessel was degassed/purged a further three times. The reaction mixture was then heated at 80° C. for 24 h. The crude material was purified by Combiflash ISCO chromatography (DCM:MeOH, 0 to 5%, 30 mins) to yield 7-fluoro-2-(2-methyl-[1,2,4]triazolo[1,5-b]pyridazin-6-yl)pyrido[1,2-a]pyrimidin-4-one (260 mg, 878 mol, 21.1%, m/z: 297.1 [M+H]$^+$) as a light yellow solid.

Pyridopyrimidinone Intermediate (VI-3)

7-fluoro-9-methyl-2-(2-methyl-[1,2,4]triazolo[1,5-b]pyridazin-6-yl) pyrido[1,2-a]pyrimidin-4-one

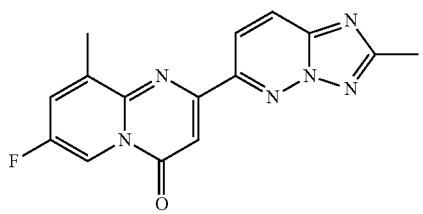 [SMILES: Cc1nc2ccc(-c3cc(=O)n4cc(F)cc(C)c4n3)nn2n1]

Part 1: 2-chloro-7-fluoro-9-methyl-pyrido[1,2-a]pyrimidin-4-one

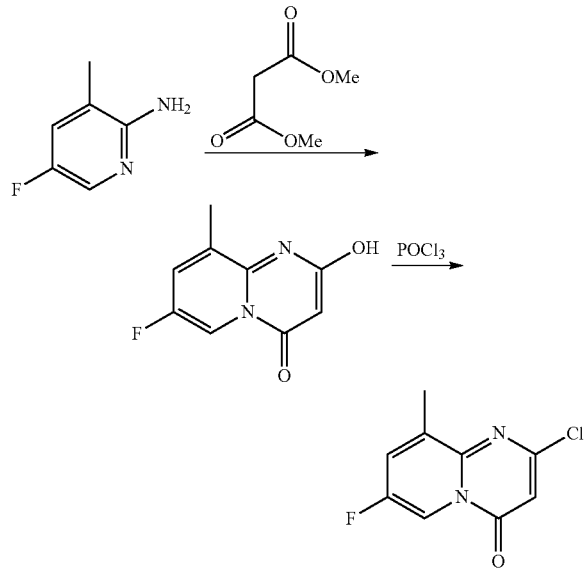

1a) 7-fluoro-2-hydroxy-9-methyl-pyrido[1,2-a]pyrimidin-4-one

A mixture of 5-fluoro-3-methylpyridin-2-amine (3.3 g, 26.2 mmol) and dimethyl malonate (15.0 mL, 0.13 mol, 5.0 eq.) was heated at 210° C. for 1.5 h. After cooling to room temperature, the precipitate was filtered and washed with ACN (3×) to give 7-fluoro-2-hydroxy-9-methyl-pyrido[1,2-a]pyrimidin-4-one as a dark solid (2.3 g), which was used directly in the next step. MS m/z 195.1 [M+H]$^+$.

1b) 2-chloro-7-fluoro-9-methyl-pyrido[1,2-a]pyrimidin-4-one

A mixture of crude 7-fluoro-2-hydroxy-9-methyl-pyrido[1,2-a]pyrimidin-4-one (2.3 g, 11.8 mmol) in POCl$_3$ (7.7 mL, 82.9 mmol) and DIPEA (2.07 mL, 11.8 mmol) was heated at 110° C. for 15 h. The volatiles were removed and the residue was treated with ice-water, washed with water (3×) and dried to give a brown solid. The crude brown solid was purified by column chromatography (SiO$_2$, 5% MeOH in DCM) to give 2-chloro-7-fluoro-9-methyl-pyrido[1,2-a]pyrimidin-4-one as a yellow solid (1.77 g, 70% over 2 steps), MS m/z 213.1 [M+H]$^+$.

Part 2: 7-fluoro-9-methyl-2-(2-methyl-[1,2,4]triazolo[1,5-b]pyridazin-6-yl)pyrido[1,2-a]pyrimidin-4-one

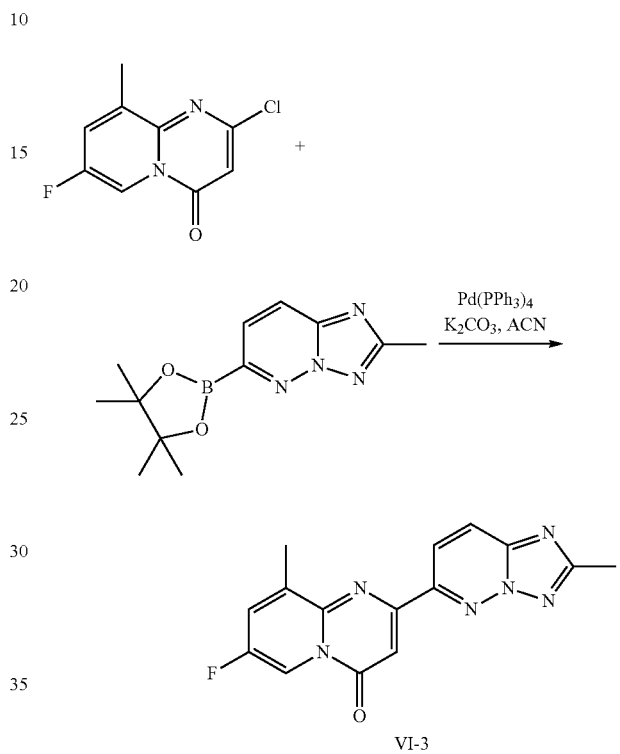

VI-3

To a 100 mL four-necked flask, 2-methyl-6-(4,4,5,5-tetramethyl-1,3,2-dioxaborolan-2-yl)-[1,2,4]triazolo[1,5-b]pyridazine (1.3 g, 4.99 mmol, 1.1 eq.), 2-chloro-7-fluoro-9-methyl-4H-pyrido[1,2-a]pyrimidin-4-one (0.964 g, 4.53 mmol, 1 eq.), potassium carbonate 2M (4.53 ml, 9.07 mmol, 2 eq.) and ACN (38.8 ml) were added. The reaction vessel was degassed and purged with argon (×5). Tetrakis(triphenylphosphine)palladium (0) (524 mg, 453 μmol, 0.1 eq.) was then added and the reaction vessel was degassed a further three times. The reaction mixture was then heated at 80° C. for 20 h. The reaction mixture was then concentrated in vacuo. The crude material was purified by column chromatography (SiO$_2$, 98:2 DCM:MeOH), then trituration in Et$_2$O (×4) and Et$_2$O/EtOAc (5:1 mixture) yielded 7-fluoro-9-methyl-2-(2-methyl-[1,2,4]triazolo[1,5-b]pyridazin-6-yl)pyrido[1,2-a]pyrimidin-4-one (221 mg, 0.712 mmol, 15.7%, m/z: 311.1 [M+H]$^+$) as a yellow solid.

General Procedure 1 for Boc Deprotection

To a stirred solution of a boc-protected amino derivative (0.089 mmol) in dichloromethane (5 mL), TFA (4.48 mmol, 50 eq.) was added dropwise over 2 minutes. The reaction mixture was stirred at RT for 1 hour. The reaction mixture was then concentrated in vacuo, then triturated in Et$_2$O (×2) to yield the product as its TFA salt.

Example 1

2-(2-methyl-[1,2,4]triazolo[1,5-a]pyrimidin-6-yl)-7-piperazin-1-yl-pyrido[1,2-a]pyrimidin-4-one

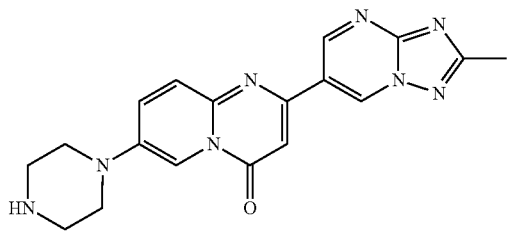 [SMILES: Cc1nc2ncc(-c3cc(=O)n4cc(N5CCNCC5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 40 mg, 0.135 mmol) and piperazine (34.9 mg, 0.405 mmol, 3 eq.) were stirred in DMSO (12 ml) at 120° C. for 90 minutes and 60° C. over the night. The solvent was removed under high vacuum. The crude was purified by column chromatography (SiO₂, DCM/MeOH/NH4OH=8.9/1/0.1 to 9/1) to afford the title product as a light yellow solid. MS m/z 363.2 [M+H]+.

Example 2

7-[(3R,5S)-3,5-dimethylpiperazin-1-yl]-2-(2-methyl-[1,2,4]triazolo[1,5-a]pyrimidin-6-yl)pyrido[1,2-a]pyrimidin-4-one

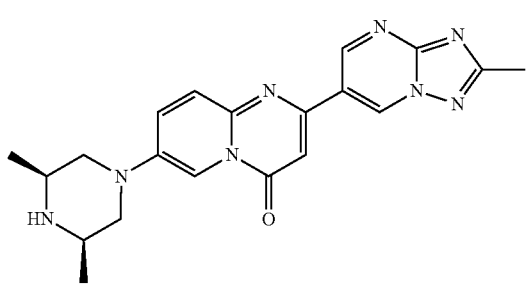

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 70 mg, 0.236 mmol) and (2S,6R)-2,6-dimethylpiperazine (80.9 mg, 0.709 mmol, 3 eq.) were stirred in DMSO (2 ml) at 80° C. over three days. The crude was purified by preparative HPLC to afford the title product (30 mg, 33%) as a yellow solid. MS m/z 391.5 [M+H]+.

Example 3

7-[(3R)-3-(dimethylamino)pyrrolidin-1-yl]-2-(2-methyl-[1,2,4]triazolo[1,5-a]pyrimidin-6-yl)pyrido[1,2-a]pyrimidin-4-one

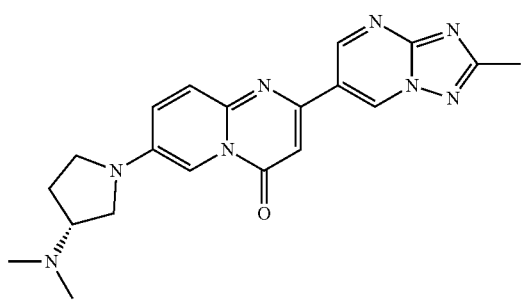

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 50 mg, 0.169 mmol) and (R)—N,N-dimethylpyrrolidin-3-amine (57.8 mg, 0.506 mmol, 3 eq.) were stirred in DMSO (2 ml) at 120° C. for 3 hours and at 60° C. overnight. The crude was purified by preparative HPLC to afford the title product (22 mg, 32%) as a green solid. MS m/z 391.3 [M+H]+.

Example 4

7-(4-methyl-1,4-diazepan-1-yl)-2-(2-methyl-[1,2,4]triazolo[1,5-a]pyrimidin-6-yl)pyrido[1,2-a]pyrimidin-4-one

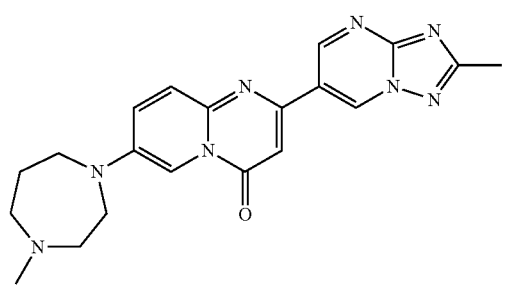 [SMILES: Cc1nc2ncc(-c3cc(=O)n4cc(N5CCCN(C)CC5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 50 mg, 0.169 mmol), 1-methyl-1,4-diazepane (58 mg, 0.506 mmol, 3.0 eq.) were stirred in DMSO (3 ml) at 120° C. for 6 hours and then 80° C. for 3 days. The reaction mixture was then triturated in DMSO (×2) and Et₂O (×2) to afford the title product (20.1 mg, 30%) as a solid. MS m/z 391.3 [M+H]+.

Example 5

7-(2,7-diazaspiro[3.5]nonan-2-yl)-2-(2-methyl-[1,2,4]triazolo[1,5-a]pyrimidin-6-yl)pyrido[1,2-a]pyrimidin-4-one

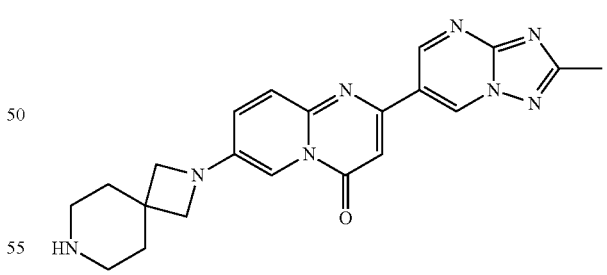

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 50 mg, 0.169 mmol), TEA (0.35 mL, 2.53 mmol, 15 eq.) and tert-butyl 2,7-diazaspiro[3.5]nonane-7-carboxylate hydrochloride (133 mg, 0.506 mmol, 3 eq.) were stirred in DMSO (2 ml) at 80° C. for 1 hour, then 100° C. for 1 hour, and then 120° C. for 3 hours, then at 60° C. overnight. Then at 120° C. for 6 hours, then at 80° C. over the weekend. The precipitating solid was filtered and triturated with diethylether.

The isolated solid was then treated following the General Procedure 1 for Boc deprotection to afford the product 2-(2-methyl-[1,2,4]triazolo[1,5-a]pyrimidin-6-yl)-7-(2,7-diazaspiro[3.5]nonan-2-yl)-4H-pyrido[1,2-a]pyrimidin-4-one 2,2,2-trifluoroacetate (28.3 mg, 0.055 mmol, 61.2% yield) as a yellow oil. MS m/z 403.3 [M+H]⁺.

Example 6

7-(3,3-dimethylpiperazin-1-yl)-2-(2-methyl-[1,2,4]triazolo[1,5-a]pyrimidin-6-yl)pyrido[1,2-a]pyrimidin-4-one

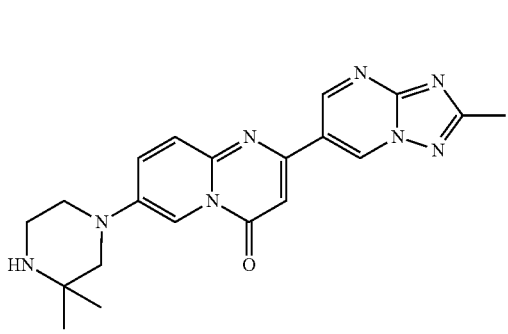 [SMILES: Cc1nc2ncc(-c3cc(=O)n4cc(N5CCNC(C)(C)C5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 50 mg, 0.169 mmol), DIPEA (0.05 mL, 0.29 mmol, 1.0 eq.) and 2,2-dimethylpiperazine (57.8 mg, 0.506 mmol, 3.0 eq.) were stirred in DMSO (2 ml) at 120° C. for 24 hours. The crude was purified by preparative HPLC to afford the title product (19 mg, 29%) as a yellow solid. MS m/z 391.3 [M+H]⁺.

Example 7

7-(2,6-diazaspiro[3.3]heptan-2-yl)-2-(2-methyl-[1,2,4]triazolo[1,5-a]pyrimidin-6-yl)pyrido[1,2-a]pyrimidin-4-one

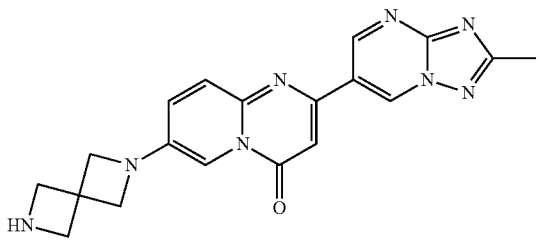 [SMILES: Cc1nc2ncc(-c3cc(=O)n4cc(N5CC6(CNC6)C5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 50 mg, 0.169 mmol), TEA (85.4 mg, 118 μl, 0.844 mmol, 5 eq.) and tert-butyl 2,6-diazaspiro[3.3]heptane-2-carboxylate hydrochloride (119 mg, 0.506 mmol, 3 eq.) were stirred in DMSO (2 ml) at 120° C. for 24 hours. The solvent was removed under high vacuum. The crude was purified by column chromatography (SiO₂, DCM/MeOH=98/2).

The isolated solid was then treated following the General Procedure 1 for Boc deprotection to afford the product 2-(2-methyl-[1,2,4]triazolo[1,5-a]pyrimidin-6-yl)-7-(2,6-diazaspiro[3.3]heptan-2-yl)-4H-pyrido[1,2-a]pyrimidin-4-one 2,2,2-trifluoroacetate (14.9 mg, 0.031 mmol, 92.2% yield) as a yellow solid. MS m/z 375.2 [M+H]⁺.

Example 8

2-(2,8-7-(2-methyl-1,3,3a,4,6,6a-hexahydropyrrolo[3,4-c]pyrrol-5-yl)-2-(2-methyl-[1,2,4]triazolo[1,5-a]pyrimidin-6-yl)pyrido[1,2-a]pyrimidin-4-one

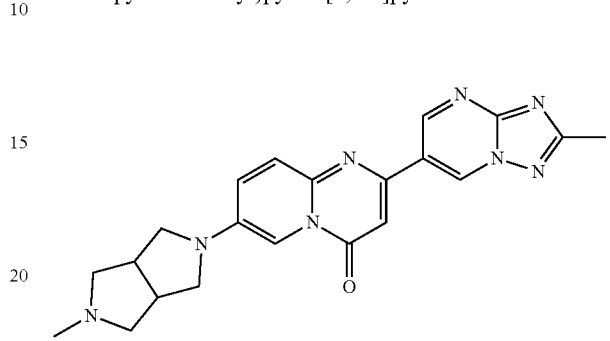

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 30 mg, 0.101 mmol), and 2-methyloctahydropyrrolo[3,4-c]pyrrole (38.3 mg, 0.304 mmol, 3 eq.) were stirred in DMSO (2 ml) at 120° C. for 24 hours. The crude was purified by preparative HPLC to afford the title product (7 mg, 17%) as a yellow solid. MS m/z 403.4 [M+H]⁺.

Example 9

7-(3,6-diazabicyclo[3.2.0]heptan-3-yl)-2-(2-methyl-[1,2,4]triazolo[1,5-a]pyrimidin-6-yl)pyrido[1,2-a]pyrimidin-4-one

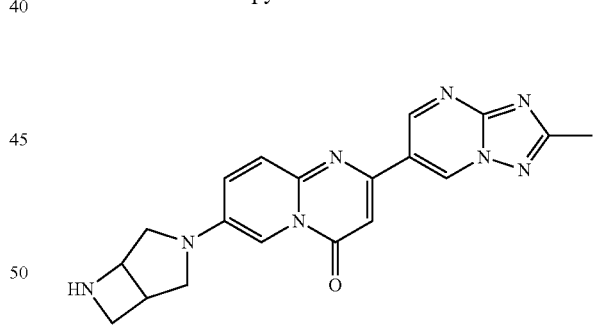

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 25.4 mg, 0.169 mmol, 1 eq.), and tert-butyl 3,6-diazabicyclo[3.2.0]heptane-6-carboxylate (100 mg, 0.506 mmol, 3 eq.) were stirred in DMSO (2 ml) at 120° C. for 48 hours. The crude was purified by preparative HPLC.

The isolated solid was then treated following the General Procedure 1 for Boc deprotection to afford the product 7-(3,6-diazabicyclo[3.2.0]heptan-3-yl)-2-(2-methyl-[1,2,4]triazolo[1,5-a]pyrimidin-6-yl)-4H-pyrido[1,2-a]pyrimidin-4-one 2,2,2-trifluoroacetate (12.4 mg, 0.025 mmol, 73.9% yield) as a yellow solid.

Example 10

7-[4-(azetidin-3-yl)piperazin-1-yl]-2-(2-methyl-[1,2,4]triazolo[1,5-a]pyrimidin-6-yl)pyrido[1,2-a]pyrimidin-4-one

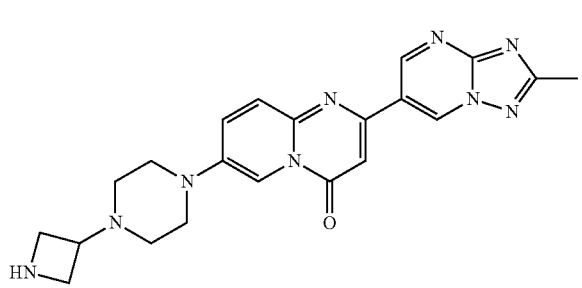 [SMILES: Cc1nc2ncc(-c3cc(=O)n4cc(N5CCN(C6CNC6)CC5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 50 mg, 0.169 mmol, and tert-butyl 3-(piperazin-1-yl)azetidine-1-carboxylate (122 mg, 0.506 mmol, 3 eq.) were stirred in DMSO (2 ml) at 120° C. for 96 hours. The crude was purified by preparative HPLC.

The isolated solid was then treated following the General Procedure 1 for Boc deprotection to afford the product 7-(4-(azetidin-3-yl)piperazin-1-yl)-2-(2-methyl-[1,2,4]triazolo[1,5-a]pyrimidin-6-yl)-4H-pyrido[1,2-a]pyrimidin-4-one 2,2,2-trifluoroacetate (18.8 mg, 0.035 mmol, 98.4% yield) as a yellow solid. MS m/z 418.3 [M+H]$^+$.

Example 11

7-[(3S,5S)-3,5-dimethylpiperazin-1-yl]-2-(2-methyl-[1,2,4]triazolo[1,5-a]pyrimidin-6-yl)pyrido[1,2-a]pyrimidin-4-one

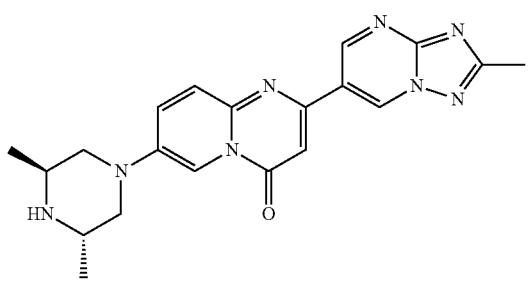

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 30 mg, 0.101 mmol), and (2S,6S)-2,6-dimethylpiperazine dihydrochloride (56.8 mg, 0.304 mmol, 3 eq.) were stirred in DMSO (2 ml) at 120° C. for 96 hours. The crude was purified by preparative HPLC to afford the title product (8 mg, 21%) as an orange solid. MS m/z 391.2 [M+H]$^+$.

Example 12

7-[4-(pyrrolidin-1-ylmethyl)-1-piperidyl]-2-(2-methyl-[1,2,4]triazolo[1,5-a]pyrimidin-6-yl)-pyrido[1,2-a]pyrimidin-4-one

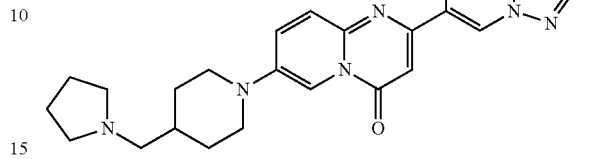

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 30 mg, 0.101 mmol), and 4-(pyrrolidin-1-ylmethyl)piperidine dihydrochloride (73.3 mg, 0.304 mmol, 3 eq.) were stirred in DMSO (2 ml) at 120° C. for 24 hours. The solution was filtered, and the solid was triturated in Et$_2$O (×2) to afford the title product (6 mg, 13%) as a yellow solid. MS m/z 445.4 [M+H]$^+$.

Example 13

7-(4,7-diazaspiro[2.5]octan-7-yl)-2-(2-methyl-[1,2,4]triazolo[1,5-a]pyrimidin-6-yl)pyrido[1,2-a]pyrimidin-4-one

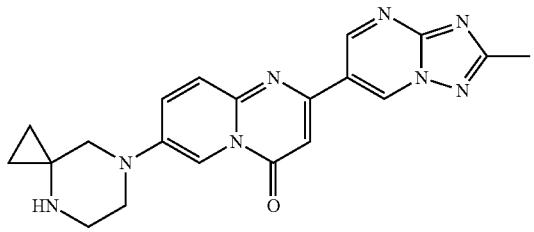 [SMILES: Cc1nc2ncc(-c3cc(=O)n4cc(N5CCNC6(CC6)C5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1); 50 mg, 0.169 mmol), 4,7-diazaspiro[2.5]octane dihydrochloride (93.7 mg, 0.506 mmol, 3 eq.) and TEA (171 mg, 235 µl, 1.69 mmol, 10 eq.) were stirred in DMSO (2 ml) at 120° C. for 24 hours. The crude was purified by preparative HPLC to afford the title product (6 mg, 10%) as a yellow solid. MS m/z 389.2 [M+H]$^+$.

Example 14

7-[4-(oxetan-3-yl)piperazin-1-yl]2-(2-methyl-[1,2,4]triazolo[1,5-a]pyrimidin-6-yl)pyrido[1,2-a]pyrimidin-4-one

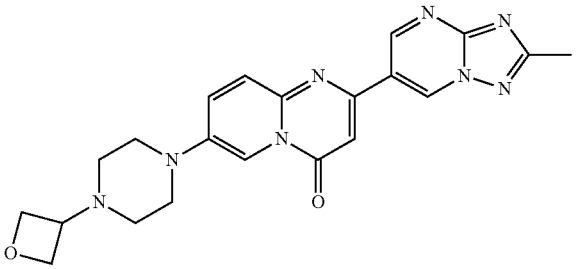 [SMILES: Cc1nc2ncc(-c3cc(=O)n4cc(N5CCN(C6COC6)CC5)ccc4n3)cn2n1]

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 30 mg, 0.101 mmol), and 1-(oxetan-3-yl)piperazine (43.2 mg, 0.304 mmol, 3 eq.) were dissolved in DMSO (2 ml). The reaction mixture was heated at 120° C. for 48 hours. The crude was purified by preparative HPLC to afford the title product (12 mg, 28%) as a light yellow solid. MS m/z 419.3 [M+H]$^+$.

Example 15

9-methyl-7-piperazin-1-yl-2-(2-methyl-[1,2,4]triazolo[1,5-b]pyridazin-6-yl)pyrido[1,2-a]pyrimidin-4-one

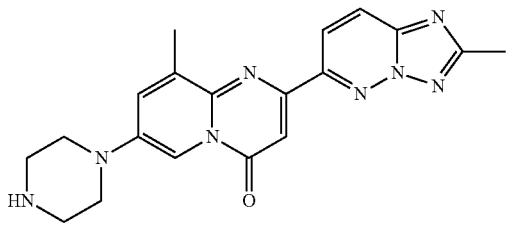 [SMILES: Cc1nc2ccc(-c3cc(=O)n4cc(N5CCNCC5)cc(C)c4n3)nn2n1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 10.8 mg, 0.035 mmol), piperazine (8.99 mg, 0.104 mmol, 3 eq.) and TEA (17.6 mg, 24.3 µl, 0.174 mmol, 5 eq.) were stirred in a sealed tube with DMSO (1 ml) at 120° C. for 12 hours. The reaction mixture was concentrated in vacuo and redissolved in MeOH. The crude was purified by column chromatography (SiO$_2$, DCM/MeOH=80/20) to afford the title product (11 mg, 86%) as an orange solid. MS m/z 377.2 [M+H]$^+$.

Example 16

7-[(3S)-3-methylpiperazin-1-yl]-2-(2-methyl-[1,2,4]triazolo[1,5-a]pyrimidin-6-yl)pyrido[1,2-a]pyrimidin-4-one

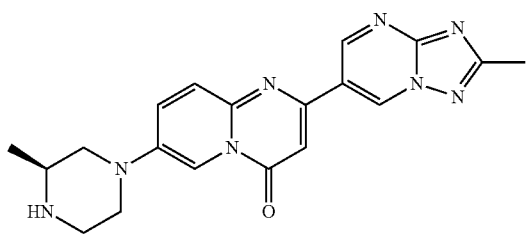

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 30 mg, 0.101 mmol), (S)-2-methylpiperazine (30.4 mg, 0.304 mmol, 3 eq.) and TEA (51.2 mg, 70.6 µl, 0.506 mmol, 5 eq.) were dissolved in DMSO (2 ml). The reaction mixture was heated at 120° C. for 12 hours. The crude was filtered to afford the title product (29 mg, 77%) as a yellow solid. MS m/z 377.2 [M+H]$^+$.

Example 17

7-[(3R)-3-methylpiperazin-1-yl]-2-(2-methyl-[1,2,4]triazolo[1,5-b]pyridazin-6-yl)pyrido[1,2-a]pyrimidin-4-one

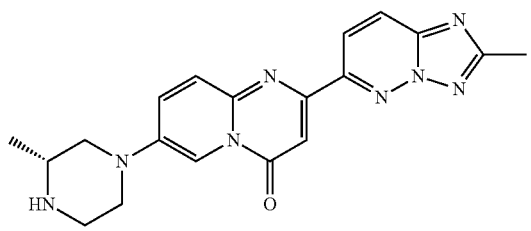

In a sealed tube 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol, 1 eq.) and (R)-2-methylpiperazine (20.3 mg, 0.203 mmol, 3 eq.) were stirred in DMSO (1 ml) at 120° C. over the night. The solvent was removed under high vacuum. The crude was purified by column chromatography (SiO$_2$, DCM/MeOH=90/10 to 80/20) to afford the title product (9 mg, 35%) as a yellow solid. MS m/z 377.2 [M+H]$^+$.

Example 18

7-[(3S)-3-methylpiperazin-1-yl]-2-(2-methyl-[1,2,4]triazolo[1,5-b]pyridazin-6-yl)pyrido[1,2-a]pyrimidin-4-one

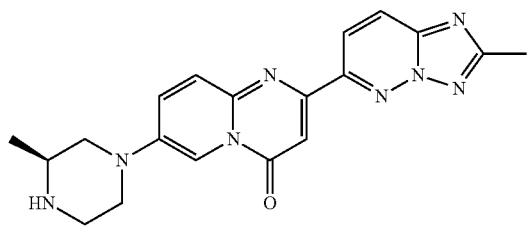

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (17.1 mg, 23.5 µl, 0.169 mmol, 5 eq.) and (R)-2-methylpiperazine (20.3 mg, 0.203 mmol, 3 eq.) were combined in DMSO (0.5 ml) and heated at 120° C. for 2 hours and 30 minutes. The precipitating product was filtered and triturated with diethylether to afford the title product (6 mg, 47%) as a brown solid. MS m/z 377.3 [M+H]$^+$.

Example 19

7-piperazin-1-yl-2-(2-methyl-[1,2,4]triazolo[1,5-b]pyridazin-6-yl)pyrido[1,2-a]pyrimidin-4-one

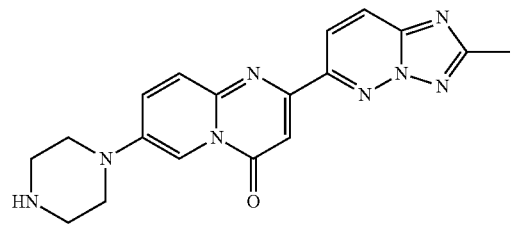 [SMILES: Cc1nc2ccc(-c3cc(=O)n4cc(N5CCNCC5)ccc4n3)nn2n1]

In a sealed tube, 7-fluoro-2-(2-methyl-[1,2,4]triazolo[1,5-b]pyridazin-6-yl)-4H-pyrido[1,2-a]pyrimidin-4-one (intermediate VI-2, 13 mg, 0.044 mmol), TEA (22.2 mg, 30.6 μl, 0.219 mmol, eq.) and piperazine (11.3 mg, 0.132 mmol, 3 eq.) were stirred in DMSO (0.5 ml) at 120° C. for 90 minutes. The precipitating product was filtered and triturated with diethylether to afford the title product (5.2 mg, 33%) as a brown solid. MS m/z 363 [M+H]+.

Example 20

7-(4-methyl-1,4-diazepan-1-yl)-2-(2-methyl-[1,2,4]triazolo[1,5-b]pyridazin-6-yl)pyrido[1,2-a]pyrimidin-4-one

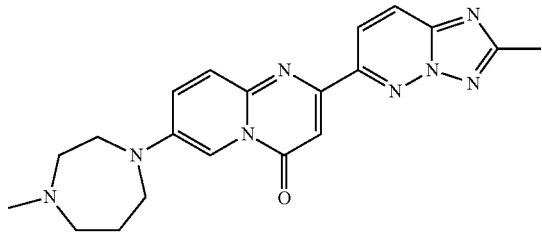

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 17 mg, 0.057 mmol), TEA (29 mg, 40 μl, 0.287 mmol, 5 eq.) and 1-methyl-1,4-diazepane (19.7 mg, 0.172 mmol, 3 eq.) were stirred in DMSO (0.5 ml) at 120° C. for 4.5 hours. The precipitating product was filtered and triturated with diethylether to afford the title product (8.5 mg, 38%) as a brown solid. MS m/z 391.2 [M+H]+.

Example 21

7-(6-methyl-2,6-diazaspiro[3.3]heptan-2-yl)-2-(2-methyl-[1,2,4]triazolo[1,5-a]pyrimidin-6-yl)pyrido[1,2-a]pyrimidin-4-one

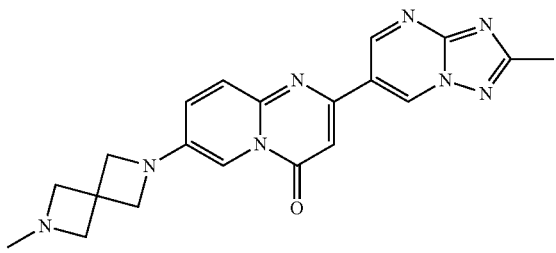

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 30 mg, 0.101 mmol), TEA (154 mg, 212 μl, 1.52 mmol, eq.) and 2-methyl-2,6-diazaspiro[3.3]heptane dihydrochloride (56.2 mg, 0.304 mmol, 3 eq.) were stirred in DMSO (2 ml) and heated at 120° C. for 24 hours. The crude was purified by preparative HPLC to afford the title product (6.2 mg, 16%) as a yellow solid. MS m/z 389.2 [M+H]+.

Example 22

7-[(3R,5S)-3,5-dimethylpiperazin-1-yl]-2-(2-methyl-[1,2,4]triazolo[1,5-b]pyridazin-6-yl)pyrido[1,2-a]pyrimidin-4-one

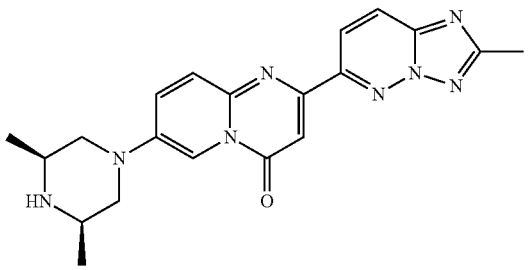

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 17 mg, 0.057 mmol), TEA (29 mg, 40 μl, 0.287 mmol, 5 eq.) and (2S,6R)-2,6-dimethylpiperazine (19.7 mg, 0.172 mmol, 3 eq.) were stirred in DMSO (0.5 ml) at 120° C. for 7 hours. The precipitating solid was filtered and triturated with diethyl ether/methanol 95/5. This solid was purified by column chromatography (SiO2, DCM/MeOH=9/1) to afford the title product (4.8 mg, 21%) as a yellow solid. MS m/z 391.2 [M+H]+.

Example 23

7-(4-methylpiperazin-1-yl)-2-(2-methyl-[1,2,4]triazolo[1,5-a]pyrimidin-6-yl)pyrido[1,2-a]pyrimidin-4-one

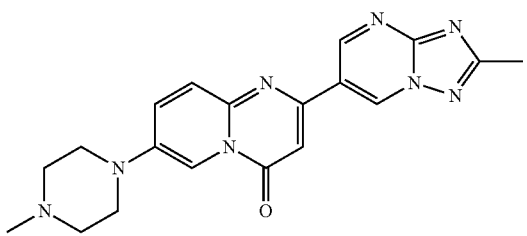

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 30 mg, 0.101 mmol), TEA (51.2 mg, 70.6 μl, 0.506 mmol, 5 eq.) and 1-methylpiperazine (30.4 mg, 0.304 mmol, 3 eq.) were stirred in DMSO (2 ml) at 120° C. for 24 hours. The precipitating product was filtered and triturated with diethylether to afford the title product (14.9 mg, 39%) as a yellow solid. MS m/z 377.2 [M+H]+.

Example 24

7-[(3R)-3-methylpiperazin-1-yl]-2-(2-methyl-[1,2,4]triazolo[1,5-a]pyrimidin-6-yl)pyrido[1,2-a]pyrimidin-4-one

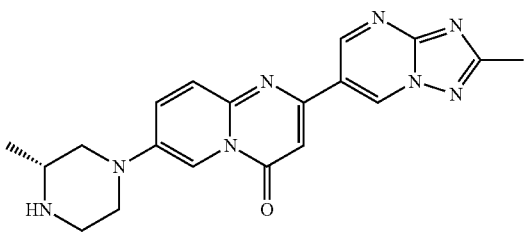

In a sealed tube, 7-fluoro-2-(2-methyl-[1,2,4]triazolo[1,5-a]pyrimidin-6-yl)-4H-pyrido[1,2-a]pyrimidin-4-one (Intermediate (VI-1), 30 mg, 0.101 mmol) and (R)-2-methylpiperazine (30.4 mg, 0.304 mmol, 3 eq.) were stirred in DMSO (2 ml) at 120° C. for 24 hours. The precipitating product was filtered and triturated with diethylether to afford the title product (21.6 mg, 57%) as a brown solid. MS m/z 377.2 [M+H]+.

Example 25

9-methyl-7-(4-methyl-1,4-diazepan-1-yl)-2-(2-methyl-[1,2,4]triazolo[1,5-b]pyridazin-6-yl)pyrido[1,2-a]pyrimidin-4-one

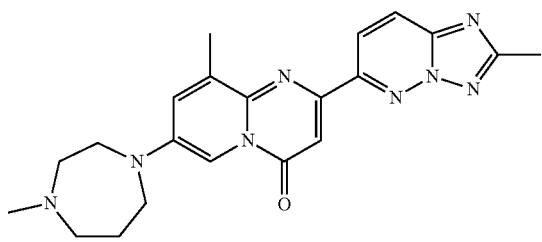

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), TEA (32.6 mg, 44.9 µl, 0.322 mmol, 5 eq.) and 1-methyl-1,4-diazepane (22.1 mg, 0.193 mmol, 3 eq.) were stirred in DMSO (1.2 ml) at 120° C. for 8 hours. The precipitating product was filtered and triturated with diethylether to afford the title product (7.1 mg, 27%) as a yellow solid. MS m/z 405.3 [M+H]+.

Example 26

7-[(3R,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one

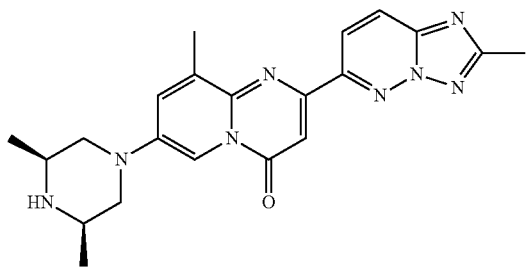

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 30 mg, 0.097 mmol), TEA (48.9 mg, 67.4 µl, 0.483 mmol, 5 eq.) and (2S,6R)-2,6-dimethylpiperazine (33.1 mg, 0.290 mmol, 3 eq.) were stirred in DMSO (1.5 ml) at 120° C. for 24 hours. The crude was purified by column chromatography (SiO2, DCM/MeOH=90/10) to afford the title product (30 mg, 76%) as a brown solid. MS m/z 405.3 [M+H]+.

Example 27

9-methyl-7-(4-methylpiperazin-1-yl)-2-(2-methyl-[1,2,4]triazolo[1,5-b]pyridazin-6-yl)pyrido[1,2-a]pyrimidin-4-one

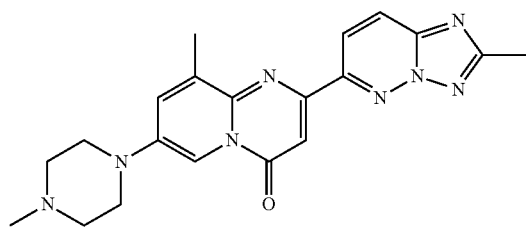

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), TEA (32.6 mg, 44.9 µl, 0.322 mmol, 5 eq.) and 1-methylpiperazine (19.4 mg, 0.193 mmol, 3 eq.) were stirred in DMSO (1.2 ml) at 120° C. for 8 hours. The crude was purified by column chromatography (SiO2, DCM/MeOH=90/10) to afford the title product (15.4 mg, 61%) as a yellow solid. MS m/z 391.2 [M+H]+.

Example 28

7-(3,3-dimethylpiperazin-1-yl)-9-methyl-2-(2-methyl-[1,2,4]triazolo[1,5-b]pyridazin-6-yl)pyrido[1,2-a]pyrimidin-4-one

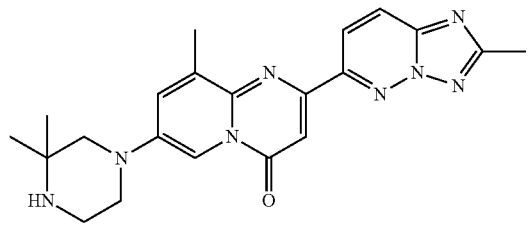

In a sealed tube, 7-fluoro-9-methyl-2-(2-methyl-[1,2,4]triazolo[1,5-b]pyridazin-6-yl)-4H-pyrido[1,2-a]pyrimidin-4-one (intermediate VI-3, 20 mg, 0.064 mmol), TEA (32.6 mg, 44.9 µl, 0.322 mmol, 5 eq.) and 2,2-dimethylpiperazine (22.1 mg, 0.193 mmol, 3 eq.) were stirred in DMSO (1.2 ml) at 120° C. for 15 hours. The crude was purified by preparative HPLC to afford the title product (10 mg, 39%) as an orange solid. MS m/z 405.3 [M+H]+.

Example 29

7-[(3aS,6aR)-2-methyl-1,3,3a,4,6,6a-hexahydropyrrolo[3,4-c]pyrrol-5-yl]-9-methyl-2-(2-methyl-[1,2,4]triazolo[1,5-b]pyridazin-6-yl)pyrido[1,2-a]pyrimidin-4-one

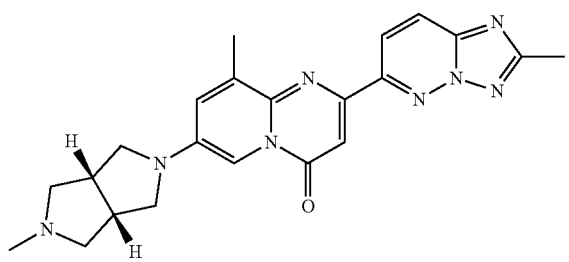

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), TEA (32.6 mg, 44.9 µl, 0.322 mmol, 5 eq.) and 2-methyloctahydropyrrolo[3,4-c]pyrrole (24.4 mg, 0.193 mmol, 3 eq.) were stirred in DMSO (1.2 ml) at 120° C. for 3 hours. The precipitating product was filtered and triturated with diethylether to afford the title product (20.2 mg, 75%) as a yellow solid. MS m/z 417.3 [M+H]$^+$.

Example 30

7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one

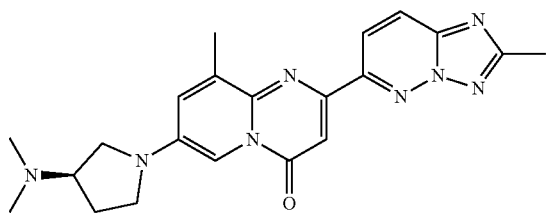

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), TEA (32.6 mg, 44.9 µl, 0.322 mmol, 5 eq.) and (R)—N,N-dimethylpyrrolidin-3-amine (22.1 mg, 0.193 mmol, 3 eq.) were stirred in DMSO (1.2 ml) at 120° C. for 3 hours. The precipitating product was filtered and triturated with diethylether to afford the title product (20.7 mg, 80%) as a yellow solid. MS m/z 405.3 [M+H]$^+$.

Example 31

9-methyl-7-[4-(oxetan-3-yl)piperazin-1-yl]-2-(2-methyl-[1,2,4]triazolo[1,5-b]pyridazin-6-yl)pyrido[1,2-a]pyrimidin-4-one

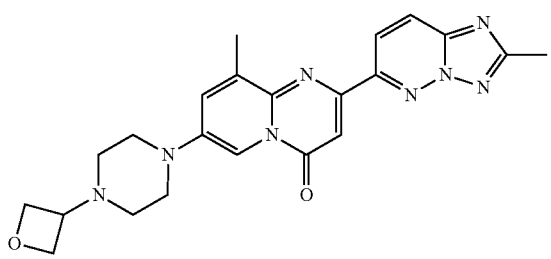 [SMILES: Cc1nc2ccc(-c3cc(=O)n4cc(N5CCN(C6COC6)CC5)cc(C)c4n3)nn2n1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), (32.6 mg, 44.9 µl, 0.322 mmol, 5 eq.) and 1-(oxetan-3-yl)piperazine (27.5 mg, 0.193 mmol, 3 eq.) were stirred in DMSO (1.2 ml) and heated at 120° C. for 12 hours. The crude was purified by preparative HPLC to afford the title product (16 mg, 57%) as a yellow solid. MS m/z 433.3 [M+H]$^+$.

Example 32

7-(4-ethylpiperazin-1-yl)-9-methyl-2-(2-methyl-[1,2,4]triazolo[1,5-b]pyridazin-6-yl)pyrido[1,2-a]pyrimidin-4-one

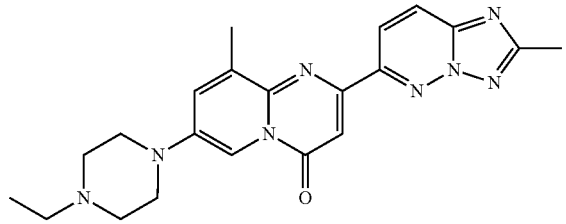 [SMILES: CCN1CCN(c2cc(C)c3nc(-c4ccc5nc(C)nn5n4)cc(=O)n3c2)CC1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3); 20 mg, 0.322 mmol), TEA (32.6 mg, 44.9 µl, 0.322 mmol, 5 eq.) and 1-ethylpiperazine (22.1 mg, 0.193 mmol, 3 eq.) were stirred in DMSO (1.2 ml) and heated at 120° C. for 12 hours. The crude was purified by preparative HPLC to afford the title product (8.5 mg, 33%) as a yellow solid. MS m/z 405.2 [M+H]$^+$.

Example 33

7-(2-methyl-1,3,3a,4,6,6a-hexahydropyrrolo[3,4-c]pyrrol-5-yl)-2-(2-methyl-[1,2,4]triazolo[1,5-b]pyridazin-6-yl)pyrido[1,2-a]pyrimidin-4-one

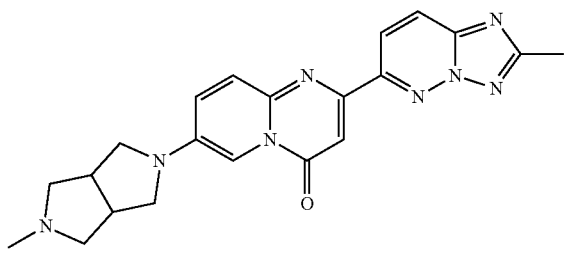

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (34.2 mg, 47 µl, 0.338 mmol, eq.) and 2-methyloctahydropyrrolo[3,4-c]pyrrole (25.6 mg, 0.203 mmol, 3 eq.) were stirred in DMSO (1.2 ml) and heated at 120° C. for 1 hour 30. The precipitating product was filtered and triturated with diethylether to afford the title product (21.8 mg, 80%) as a yellow solid. MS m/z 403.2 [M+H]$^+$.

Example 34

7-[(8aR)-3,4,6,7,8,8a-hexahydro-1H-pyrrolo[1,2-a]pyrazin-2-yl]-9-methyl-2-(2-methyl-[1,2,4]triazolo[1,5-b]pyridazin-6-yl)pyrido[1,2-a]pyrimidin-4-one

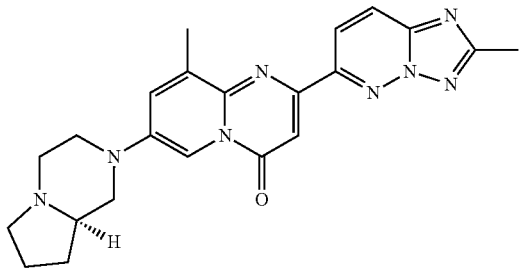 [SMILES: Cc1nc2ccc(-c3cc(=O)n4cc(N5CCN6CCC[C@@H]6C5)cc(C)c4n3)nn2n1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 18 mg, 0.058 mmol), TEA (29.4 mg, 40.4 µl, 0.290 mmol, 5 eq.) and (R)-octahydropyrrolo[1,2-a]pyrazine (22 mg, 0.174 mmol, 3 eq.) were stirred in DMSO (1.2 ml) and heated at 120° C. over the night. The precipitating product was filtered and triturated with diethylether to afford the title product (4.8 mg, 20%) as a yellow solid. MS m/z 417.3 [M+H]+.

Example 35

7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one

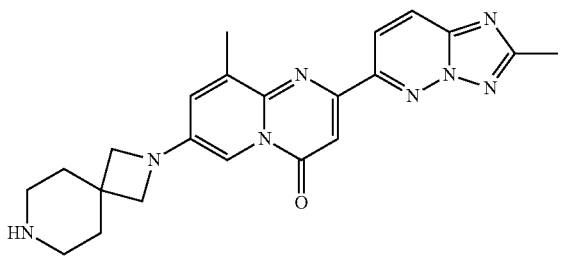 [SMILES: Cc1nc2ccc(-c3cc(=O)n4cc(N5CC6(CCNCC6)C5)cc(C)c4n3)nn2n1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 18 mg, 0.058 mmol), and tert-butyl 2,7-diazaspiro[3.5]nonane-7-carboxylate hydrochloride (45.7 mg, 0.174 mmol, 3 eq.) were stirred in DMSO (0.720 ml) and heated at 120° C. over the night. The solvent was removed under high vacuum. The residue triturated twice in methanol and twice in diethylether.

The isolated solid was then treated following the General Procedure 1 for Boc deprotection to afford the product 7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one;2,2,2-trifluoroacetic acid (2.5 mg, 0.005 mmol, 35% yield) as a yellow liquid. MS m/z 417.3 [M+H]+.

Example 36

7-[(8aR)-3,4,6,7,8,8a-hexahydro-1H-pyrrolo[1,2-a]pyrazin-2-yl]-2-(2-methyl-[1,2,4]triazolo[1,5-b]pyridazin-6-yl)pyrido[1,2-a]pyrimidin-4-one

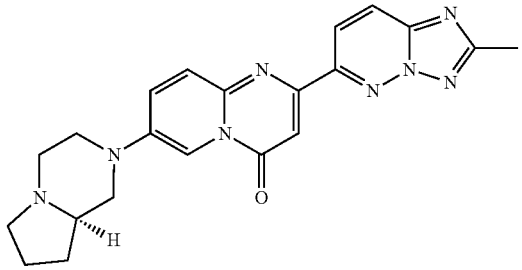 [SMILES: Cc1nc2ccc(-c3cc(=O)n4cc(N5CCN6CCC[C@@H]6C5)ccc4n3)nn2n1]

In a sealed tube, 7-fluoro-2-(2-methyl-[1,2,4]triazolo[1,5-b]pyridazin-6-yl)-4H-pyrido[1,2-a]pyrimidin-4-one (intermediate VI-2, 20 mg, 0.068 mmol), TEA (34.2 mg, 47 µl, 0.338 mmol, 5 eq.) and (R)-octahydropyrrolo[1,2-a]pyrazine (25.6 mg, 0.203 mmol, 3 eq.) were stirred in DMSO (1.2 ml) and heated at 120° C. for 24 hours. The precipitating product was filtered and triturated with diethylether to afford the title product (14.3 mg, 53%) as a brown solid. MS m/z 403.2 [M+H]+.

Example 37

7-[(3S,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one

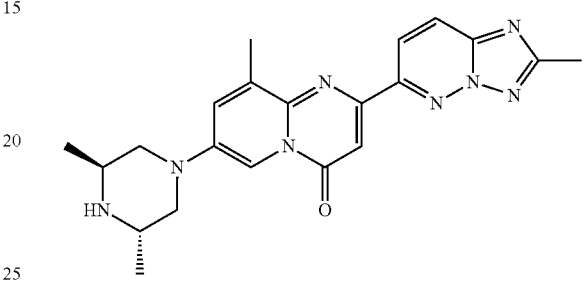

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 18 mg, 0.058 mmol), TEA (121 µl, 0.870 mmol, 15 eq.) and (2S,6S)-2,6-dimethylpiperazine dihydrochloride (32.6 mg, 0.174 mmol, 3 eq.) were stirred in DMSO (1 ml) and heated at 130° C. over the night. The precipitating solid was filtered and triturated with diethyl ether/methanol 95/5. This solid was purified by column chromatography (SiO2, DCM/MeOH=9/1) to afford the title product (3.2 mg, 14%) as a yellow solid. MS m/z 405.2 [M+H]+.

Example 38

7-(2,7-diazaspiro[3.5]nonan-2-yl)-2-(2-methyl-[1,2,4]triazolo[1,5-b]pyridazin-6-yl)pyrido[1,2-a]pyrimidin-4-one

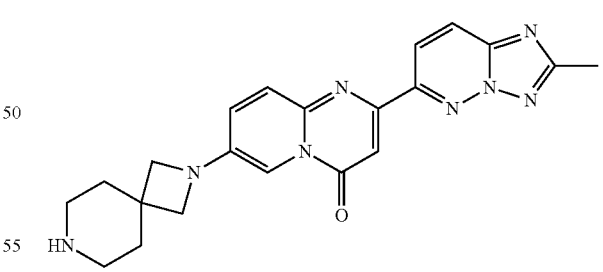

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 30 mg, 0.101 mmol), TEA (51.2 mg, 70.6 µl, 0.506 mmol, 5 eq.) and tert-butyl 2,7-diazaspiro[3.5]nonane-7-carboxylate (68.8 mg, 0.304 mmol, 3 eq.) were stirred in DMSO (1.8 ml) and heated at 120° C. for 3 hours. The precipitating solid was filtered and triturated with diethylether.

The isolated solid was then treated following the General Procedure 1 for Boc deprotection to afford the product 2-(2-methyl-[1,2,4]triazolo[1,5-b]pyridazin-6-yl)-7-(2,7-diazaspiro[3.5]nonan-2-yl)-4H-pyrido[1,2-a]pyrimidin-4-one 2,2,2-trifluoroacetate (34.5 mg, 0.067 mmol, 96% yield) as a yellow solid. MS m/z 403.2 [M+H]⁺.

Example 39

7-(4-methylpiperazin-1-yl)-2-(2-methyl-[1,2,4]triazolo[1,5-b]pyridazin-6-yl)pyrido[1,2-a]pyrimidin-4-one

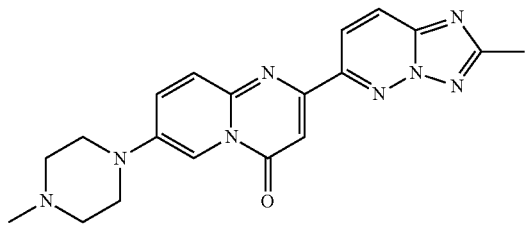

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (34.2 mg, 47 µl, 0.338 mmol, eq.) and 1-methylpiperazine (20.3 mg, 0.203 mmol, 3 eq.) were stirred in DMSO (1.2 ml) at 120° C. for 8 hours. The solvent was removed under high vacuum. The crude was purified by column chromatography (SiO₂, DCM/MeOH=95/5 to 8/2) to afford the title product (25 mg, 98%) as a yellow solid. MS m/z 377.2 [M+H]⁺.

Example 40

9-methyl-7-[(3R)-3-methylpiperazin-1-yl]-2-(2-methyl-[1,2,4]triazolo[1,5-b]pyridazin-6-yl)pyrido[1,2-a]pyrimidin-4-one

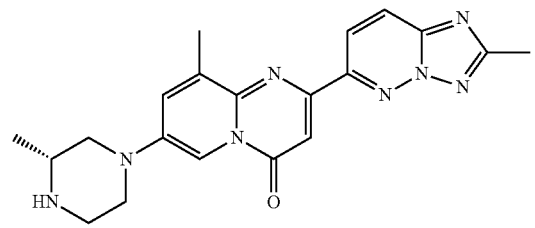

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 20 mg, 0.065 mmol), TEA (32.6 mg, 44.9 µl, 0.322 mmol, 5 eq.) and (R)-2-methylpiperazine (19.4 mg, 0.193 mmol, 3 eq.) were stirred in DMSO (1 ml) at 120° C. for 3 hours. The solvent was removed under high vacuum. The crude was purified by column chromatography (SiO₂, DCM/MeOH=95/5 to 9/1) to afford the title product (3.2 mg, 13%) as an orange solid. MS m/z 391.2 [M+H]⁺.

Example 41

7-[(3R)-3-(dimethylamino)pyrrolidin-1-yl]-2-(2-methyl-[1,2,4]triazolo[1,5-b]pyridazin-6-yl)pyrido[1,2-a]pyrimidin-4-one

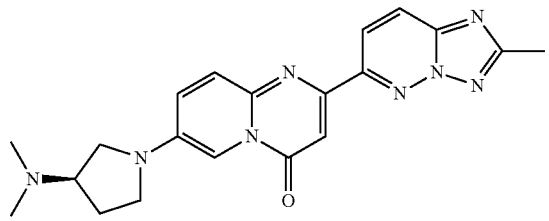

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (34.2 mg, 47 µl, 0.338 mmol, eq.) and (R)—N,N-dimethylpyrrolidin-3-amine (23.1 mg, 0.203 mmol, 3 eq.) were stirred in DMSO (1.2 ml) at 120° C. for 1 hour. The reaction mixture was filtered to afford the title product (5.4 mg, 21%) as a red solid. MS m/z 391.2 [M+H]⁺.

Example 42

7-[(3S,5S)-3,5-dimethylpiperazin-1-yl]-2-(2-methyl-[1,2,4]triazolo[1,5-b]pyridazin-6-yl)pyrido[1,2-a]pyrimidin-4-one

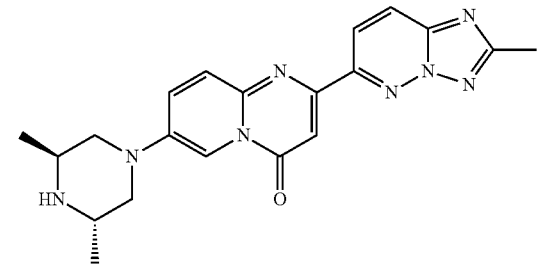

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (141 µl, 1.01 mmol, 15 eq.) and (2S,6S)-2,6-dimethylpiperazine dihydrochloride (37.9 mg, 0.203 mmol, 3 eq.) were stirred in DMSO (1.2 ml) at 120° C. for 24 hours. The solvent was removed under high vacuum. The crude was purified by column chromatography (SiO₂, DCM/MeOH=100/0 to 8/2) to afford the title product (21 mg, 79%) as a yellow solid. MS m/z 391.2 [M+H]⁺.

Example 43

7-(4-ethylpiperazin-1-yl)-2-(2-methyl-[1,2,4]triazolo[1,5-b]pyridazin-6-yl)pyrido[1,2-a]pyrimidin-4-one

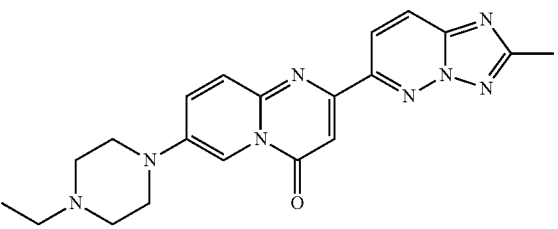 [SMILES: CCN1CCN(c2ccc3nc(-c4ccc5nc(C)nn5n4)cc(=O)n3c2)CC1]

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (34.2 mg, 47 μl, 0.338 mmol, eq.) and 1-ethylpiperazine (23.1 mg, 0.203 mmol, 3 eq.) were stirred in DMSO (1.2 ml) at 120° C. for 8 hours. The crude was purified by preparative HPLC to afford the title product (24 mg, 90%) as a yellow solid. MS m/z 391.2 [M+H]$^+$.

Example 44

7-(4,7-diazaspiro[2.5]octan-7-yl)-2-(2-methyl-[1,2,4]triazolo[1,5-b]pyridazin-6-yl)pyrido[1,2-a]pyrimidin-4-one

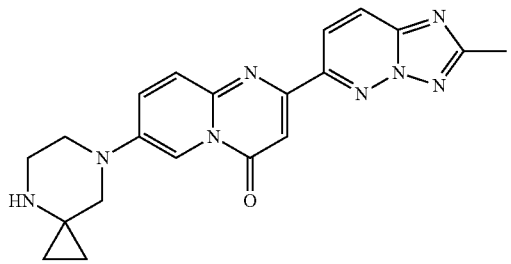 [SMILES: Cc1nc2ccc(-c3cc(=O)n4cc(N5CCNC6(CC6)C5)ccc4n3)nn2n1]

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (102 mg, 141 μl, 1.01 mmol, eq.) and 4,7-diazaspiro[2.5]octane dihydrochloride (37.5 mg, 0.203 mmol, 3 eq.) were stirred in DMSO (1.2 ml) at 120° C. for 12 hours. The crude was purified by preparative HPLC to afford the title product (26.2 mg, 21%) as a brown solid. MS m/z 389.2 [M+H]$^+$.

Example 45

9-methyl-7-[(3S)-3-methylpiperazin-1-yl]-2-(2-methyl-[1,2,4]triazolo[1,5-b]pyridazin-6-yl)pyrido[1,2-a]pyrimidin-4-one

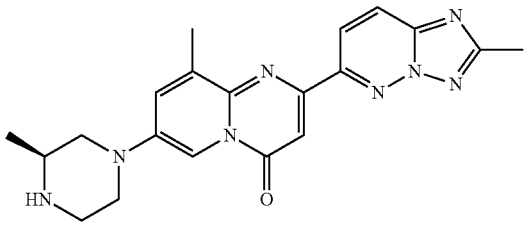

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-3), 20 mg, 0.068 mmol), TEA (32.6 mg, 45 μl, 0.322 mmol, eq.) and (R)-2-methylpiperazine (20.3 mg, 0.203 mmol, 3 eq.) were stirred in DMSO (1 ml) at 120° C. for 5 hours. The solvent was removed under high vacuum. The crude was purified by column chromatography (SiO$_2$, DCM/MeOH=95/5 to 9/1) to afford the title product (4 mg, 15%) as an orange solid. MS m/z 391.2 [M+H]$^+$.

Example 46

7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one

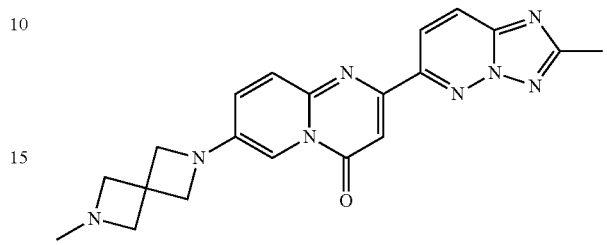

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 20 mg, 0.068 mmol), TEA (141 μl, 1.01 mmol, 15 eq.) and 2-methyl-2,6-diazaspiro[3.3]heptane dihydrochloride (37.5 mg, 0.203 mmol, 3 eq.) were stirred in DMSO (1.2 ml) at 120° C. for 8 hours. The crude was purified by preparative HPLC to afford the title product (10 mg, 39%) as a yellow solid. MS m/z 389.2 [M+H]$^+$.

Example 47

7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one

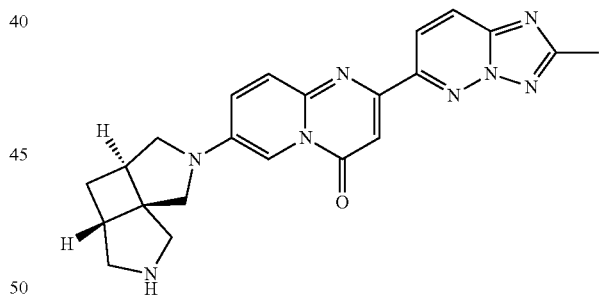

In a sealed tube, 7-fluoro-2-(2-methyl-[1,2,4]triazolo[1,5-b]pyridazin-6-yl)-4H-pyrido[1,2-a]pyrimidin-4-one (Intermediate (VI-2), 30 mg, 0.101 mmol), TEA (154 mg, 212 μl, 1.52 mmol, eq.) and (3aR,4aR,7aS)-tert-butyl hexahydro-1H-cyclobuta[1,2-c:1,4-c']dipyrrole-2(3H)-carboxylate (72.4 mg, 0.304 mmol, 3 eq.) were stirred in DMSO (1.2 ml) at 120° C. for 12 hours. The precipitated product was filtered and triturated with diethylether.

The isolated solid was then treated following the General Procedure 1 for Boc deprotection to afford the product 7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one 2,2,2-trifluoro-acetate (17.6 mg, 0.033 mmol, 95.2% yield) as a yellow solid. MS m/z 415.2 [M+H]$^+$.

Example 48

7-(2,7-diazaspiro[3.4]octan-2-yl)-9-methyl-2-(2-methyl-[1,2,4]triazolo[1,5-b]pyridazin-6-yl)pyrido[1,2-a]pyrimidin-4-one

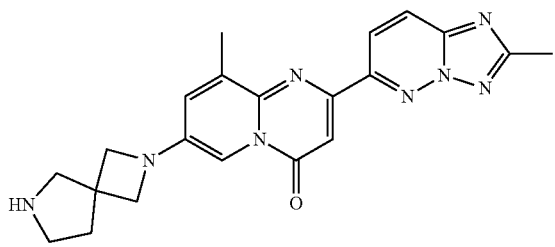 [SMILES: Cc1nc2ccc(-c3cc(=O)n4cc(N5CC6(CCNC6)C5)cc(C)c4n3)nn2n1]

In a sealed tube, 7-fluoro-9-methyl-2-(2-methyl-[1,2,4]triazolo[1,5-b]pyridazin-6-yl)-4H-pyrido[1,2-a]pyrimidin-4-one (Intermediate (VI-3), 30 mg, 0.097 mmol), TEA (34.2 mg, 47 µl, 0.338 mmol, 5 eq.) and tert-butyl 2,6-diazaspiro[3.4]octane-6-carboxylate (61.6 mg, 0.290 mmol, 3 eq.) were stirred in DMSO (1.5 ml) at 120° C. over the night. The precipitating product was filtered and triturated with diethylether.

The isolated solid was then treated following the General Procedure 1 for Boc deprotection to afford the product 7-(2,7-diazaspiro[3.4]octan-2-yl)-9-methyl-2-(2-methyl-[1,2,4]triazolo[1,5-b]pyridazin-6-yl)pyrido[1,2-a]pyrimidin-4-one;2,2,2-trifluoroacetic acid (2.5 mg, 0.005 mmol, 34.8% yield) as a brown solid. MS m/z 403.2 [M+H]$^+$.

Biological Assays

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. These examples illustrate the testing of certain compounds described herein in vitro and/or in vivo and demonstrate the usefulness of the compounds for treating of SMA by enhancing the inclusion of exon 7 of SMN2 into mRNA transcribed from the SMN2 gene. Compounds of formula (I) enhance inclusion of exon 7 of SMN2 into mRNA transcribed from the SMN2 gene and increase levels of SMN protein produced from the SMN2 gene, and thus can be used to treat SMA in a human subject in need thereof. These examples further illustrate the testing of certain compounds described herein in vitro and/or in vivo and demonstrate the usefulness of the compounds for enhancing the inclusion of exon 7 of SMN1 into mRNA transcribed from the SMN1 gene. Accordingly, compounds of formula (I) also enhance the inclusion of exon 7 of SMN1 into mRNA transcribed from the SMN1 gene and increase levels of SMN protein produced from the SMN1 gene.

Assay 1

RT-qPCR Assay for SMN2 Minigene Pre-mRNA Splicing in Cultured Cells

The reverse transcription-quantitative PCR-based (RT-qPCR) assay is used to quantify the level of the full length SMN2 minigene (referred to herein by the term "FL SMN2mini") mRNA containing SMN2 exon 7 in a HEK293H cell line stably transfected with said minigene and treated with a test compound. Materials used and respective sources are listed below in Table 1.

TABLE 1

Materials and their respective sources used in the SMN2 minigene mRNA splicing RT-qPCR assay in cultured cells.

| Material | Source |
| --- | --- |
| HEK293H cells | Thermo Fisher Scientific, Inc. (formerly Life Technologies, Inc.) Catalog No. 11631-017 |
| Cells-To-Ct lysis buffer | Thermo Fisher Scientific, Inc. (formerly Life Technologies, Inc.) part No. 4399002 |
| DMEM | Thermo Fisher Scientific, Inc. (formerly Life Technologies, Inc.) Catalog No. 11960-044 |
| 96-well flat-bottom plates | Becton Dickinson Catalog No. 353072 |
| RT-PCR Enzyme Mix | Thermo Fisher Scientific, Inc. (formerly Life Technologies, Inc.) part No. 4388520 |
| RT-PCR buffer | Thermo Fisher Scientific, Inc. (formerly Life Technologies, Inc.) part No. 4388519 |
| AgPath-ID One-Step RT-PCR kit | Thermo Fisher Scientific, Inc. (formerly Life Technologies, Inc.) part No. 4387391 |
| Thermocycler | Thermo Fisher Scientific, Inc. (formerly Life Technologies, Inc.) 7900HT |

The SMN2-A minigene construct was prepared as described in International Patent Application WO2009/151546A1 page 145 paragraph [00400] to page 147 paragraph [00412](incl. FIG. 1 and FIG. 3 therein).

HEK293H cells stably transfected with the SMN2-A minigene construct (10,000 cells/well) are seeded in 200 µL of cell culture medium (DMEM plus 10% FBS, with 200 µg/mL hygromycin) in 96-well flat-bottom plates and the plate is immediately swirled to ensure proper dispersal of cells and the formation of an even monolayer of cells. Cells are allowed to attach for 6 hours. Test compounds are serially diluted 3.16-fold in 100% DMSO to generate a 7-point concentration curve. A solution of test compound (1 µL, 200× in DMSO) is added to each cell-containing well and the plate is incubated for 24 hours in a cell culture incubator (37° C., 5% CO$_2$, 100% relative humidity). 2 replicates are prepared for each test compound concentration. The cells are then lysed in the Cells-To-Ct lysis buffer and the lysate is stored at −80° C.

Full length SMN2-A minigene and GAPDH mRNA are quantified using the primers and probes referenced in Table 2. Primer SMN Forward A (SEQ ID NO.1) hybridizes to a nucleotide sequence in exon 7 (nucleotide 22 to nucleotide 40), primer SMN Reverse A (SEQ ID NO.2) hybridizes to a nucleotide sequence in the coding sequence of Firefly luciferase, SMN Probe A (SEQ ID NO.3) hybridizes to a nucleotide sequence in exon 7 (nucleotide 50 to nucleotide 54) and exon 8 (nucleotide 1 to nucleotide 21). The combination of these three oligonucleotides detects only SMN1 or SMN2 minigenes (RT-qPCR) and will not detect endogenous SMN1 or SMN2 genes.

the 7-point concentration data generated according to the above procedure for particular compounds of the present invention.

Particular compounds of the present invention exhibit an $EC_{1-5x}$ concentration for production of full length SMN2 minigene mRNA≤5 µM.

More particular compounds of the present invention exhibit an $EC_{1-5x}$ concentration for production of full length SMN2 minigene mRNA≤1 µM.

Most particular compounds of the present invention exhibit an EC 1.5× concentration for production of full length SMN2 minigene mRNA≤0.1 µM.

TABLE 2

| Primers/Probes | Sequences | Source |
| --- | --- | --- |
| SMN Forward Primer A | SEQ ID NO. 1: GAAGGAAGGTGCTCACATT | PTC[1] |
| SMN Reverse Primer A | SEQ ID NO. 2: TCTTTATGTTTTTGGCGTCTTC | PTC[1] |
| SMN Forward Probe A | SEQ ID NO. 3: 6FAM-AAGGAGAAATGCTGGCAT AGAGCAGC-TAMRA | PTC[1] |
| hGAPDH Forward Probe | SEQ ID NO. 4: VIC-CGCCTGGTCACCAGGGCTGCT-TAMRA | LTI[2] |
| hGAPDH Forward Primer | SEQ ID NO. 5: CAACGGATTTGGTCGTATTGG | LTI[2] |
| hGAPDH Reverse Primer | SEQ ID NO. 6: TGATGGCAACAATATCCACTTTACC | LTI[2] |

[1]Primers and probes designed by PTC Therapeutics, Inc.;
[2]Commercially available from Thermo Fisher Scientific, Inc. (formerly Life Technologies, Inc.).

The SMN forward and reverse primers are used at final concentrations of 0.4 µM. The SMN probe is used at a final concentration of 0.15 µM. The GAPDH primers are used at final concentrations of 0.2 µM and the probe at 0.15 µM.

The SMN2-minigene GAPDH mix (15 µL total volume) is prepared by combining 7.5 µL of 2× RT-PCR buffer, 0.4 µL of 25× RT-PCR enzyme mix, 0.75 µL of 20×GAPDH primer-probe mix, 4.0075 µL of water, 2 µL of 10-fold diluted cell lysate, 0.06 µL of 100 µM SMN forward primer, 0.06 µL of 100 µM SMN reverse primer, and 0.225 µL of 100 µM SMN probe.

PCR is carried out at the following temperatures for the indicated time: Step 1: 48° C. (15 min); Step 2: 95° C. (10 min); Step 3: 95° C. (15 sec); Step 4: 60° C. (1 min); then repeat Steps 3 and 4 for a total of 40 cycles.

Each reaction mixture contains both SMN2-A minigene and GAPDH primers/probe sets (multiplex design), allowing simultaneous measurement of the levels of two transcripts.

The increase in the abundance of the FL SMN2mini mRNA relative to that in cells treated with vehicle control is determined from real-time PCR data using a modified ΔΔCt method (as described in Livak and Schmittgen, *Methods*, 2001, 25:402-8). The amplification efficiency E is calculated from the slope of the amplification curve for FL SMN2mini and GAPDH individually. The abundance of FL SMN2mini and GAPDH mRNA are then calculated as $(1+E)^{-Ct}$, where Ct is the threshold value for each amplicon. The abundance of FL SMN2mini mRNA is normalized to GAPDH mRNA abundance. The normalized FL SMN2mini mRNA abundance from test compound-treated samples is then divided by normalized FL SMN2mini mRNA abundance from vehicle-treated cells to determine the level of FL SMN2mini mRNA relative to vehicle control.

Table 3 provides $EC_{1-5x}$ concentrations for production of full length SMN2 minigene mRNA that was obtained from

TABLE 3

$EC_{1.5x}$ concentrations for production of full length SMN2 minigene mRNA.

| Example | $EC_{1.5x}$ minigene (µM) | Example | $EC_{1.5x}$ SMN protein (µM) |
| --- | --- | --- | --- |
| 1 | 0.0584 | 18 | 0.0176 |
| 2 | 0.067 | 19 | 0.009 |
| 3 | 0.0452 | 20 | 0.0418 |
| 4 | 0.1004 | 21 | 0.1451 |
| 5 | <0.0317 | 22 | 0.0434 |
| 6 | 0.2014 | 23 | 0.0952 |
| 7 | 0.1068 | 24 | 0.0348 |
| 8 | 0.0659 | 25 | 0.0103 |
| 9 | 0.2835 | 26 | 0.0483 |
| 10 | 5.9304 | 27 | 0.014 |
| 11 | <0.03 | 28 | 0.0096 |
| 12 | 0.1611 | 29 | 0.0008 |
| 13 | 2.5516 | 30 | 0.0065 |
| 14 | 26.1776 | 31 | 0.1301 |
| 15 | <0.03 | 32 | 0.0038 |
| 16 | 0.1147 | 33 | 0.0038 |
| 17 | 0.0191 | 34 | 0.0028 |
| | | 35 | 0.0022 |
| | | 36 | 0.0158 |
| | | 37 | 0.0026 |
| | | 38 | 0.002 |
| | | 39 | 0.0272 |
| | | 40 | 0.0088 |
| | | 41 | 0.163 |
| | | 42 | 0.0083 |
| | | 43 | 0.0328 |
| | | 44 | 0.0578 |
| | | 45 | 0.0008 |
| | | 46 | 0.003 |
| | | 47 | 0.0041 |
| | | 48 | 0.1676 |

Assay 2

SMN Protein Assay in Cultured Cells

The SMN HTRF (homogeneous time resolved fluorescence) assay is used to quantify the level of SMN protein in SMA patient fibroblast cells treated with test compounds. Materials used and respective sources are listed below in Table 4.

TABLE 4

Materials and their respective sources used in the SMN protein assay in cultured cells.

| Material | Source |
| --- | --- |
| SMA Type 1 human cells | GM03813 (Coriell Institute) |
| Protease inhibitor cocktail | Roche Applied Science Catalog No. 11836145001 |
| Anti-SMN d2 | Blue cap Cisbio Catalog No. 63IDC002-SMN |
| Anti-SMN cryptate | Red cap Cisbio Catalog No. 63IDC002-SMN |
| SMN reconstitution buffer | Cisbio Catalog No. 63IDC002-SMN-Buffer |
| DMEM | Thermo Fisher Scientific, Inc. (formerly Life Technologies, Inc.) Catalog No. 11960-044 |
| RIPA Lysis Buffer | 20 mM Tris-HCl pH 7.5, 150 mM NaCl, 1 mM EDTA, 1% Thermo Scientific NP-40 Surfact-Amps Detergent Solution (Thermo Fisher Scientific, Inc., formerly Fisher Scientific, Pittsburgh/PA), 1% Sodium deoxycholate |
| Diluent Buffer | 20 mM Tris-HCl pH 7.5, 150 mM NaCl |
| Envision Plate Reader | Perkin Elmer Model # 2103 |

Cells are thawed and cultured in DMEM-10% FBS for 72 hours. Cells are trypsinized, counted and re-suspended to a concentration of 25,000 cells/mL in DMEM-10% FBS. The cell suspensions are plated at 5,000 cells per well in a 96 well microtiter plate and incubated for 3 to hours. Test compounds are serially diluted 3.16-fold in 100% DMSO to generate a 7-point concentration curve. 1 µL of test compound solution is transferred to cell-containing wells and cells are incubated for 48 hours in a cell culture incubator (37° C., 5% $CO_2$, 100% relative humidity). Triplicate samples are set up for each test compound concentration. After 48 hours, the supernatant is removed from the wells and 25 µL of the RIPA lysis buffer, containing protease inhibitors, is added to the wells and incubated with shaking at room temperature for 1 hour. 25 µL of the diluent is added and then 35 µL of the resulting lysate is transferred to a 384-well plate, where each well contains 5 µL of the antibody solution (1:100 dilution of anti-SMN d2 and anti-SMN cryptate in SMN reconstitution buffer). The plate is centrifuged for 1 minute to bring the solution to the bottom of the wells, then incubated overnight at room temperature. Fluorescence for each well of the plate at 665 nm and 620 nm is measured on an EnVision multilabel plate reader (Perkin-Elmer).

The normalized fluorescence signal is calculated for each sample, Blank and vehicle control well by dividing the signal at 665 nm by the signal at 620 nm. Normalizing the signal accounts for possible fluorescence quenching due to the matrix effect of the lysate. The ΔF value (a measurement of SMN protein abundance as a percent value) for each sample well is calculated by subtracting the normalized average fluorescence for the Blank control wells from the normalized fluorescence for each sample well, then dividing this difference by the normalized average fluorescence for the Blank control wells and multiplying the resulting value by 100. The ΔF value for each sample well represents the SMN protein abundance from test compound-treated samples. The ΔF value for each sample well is divided by the ΔF value for the vehicle control wells to calculate the fold increase in SMN protein abundance relative to the vehicle control. Table 5 provides $EC_{1-5x}$ concentrations for SMN protein expression that was obtained from the 7-point concentration data generated according to the above procedure for particular compounds of the present invention.

Particular compounds of the present invention exhibit an $EC_{1-5x}$ concentration for SMN protein expression ≤10 µM.

More particular compounds of the present invention exhibit an $EC_{1-5x}$ concentration for SMN protein expression ≤1000 nM.

Most particular compounds of the present invention exhibit an $EC_{1-5x}$ concentration for SMN protein expression ≤100 nM.

Table 6 provides the maximum fold increase of SMN protein that was obtained from the 7-point concentration data generated according to the above procedure for particular compounds of the present invention Particular compounds of the present invention exhibit a maximum fold increase >1.5.

More particular compounds of the present invention exhibit a maximum fold increase >1.7.

Most particular compounds of the present invention exhibit a maximum fold increase >1.8.

TABLE 5

$EC_{1.5x}$ concentrations for SMN protein expression.

| Example | $EC_{1.5x}$ SMN protein (µM) |
| --- | --- |
| 1 | 0.2206 |
| 2 | 0.5082 |
| 3 | 0.5205 |
| 4 | 0.3235 |
| 5 | 0.1057 |
| 6 | 2.1472 |
| 7 | 0.2475 |
| 8 | 0.3128 |
| 9 | 2.8838 |
| 10 | 30.0328 |
| 11 | 0.1748 |
| 12 | >31.60 |
| 13 | 14.1044 |
| 14 | >31.60 |
| 15 | <0.03 |
| 16 | 0.2805 |
| 17 | 0.0932 |
| 18 | 0.0515 |
| 19 | 0.0392 |
| 20 | 0.1196 |
| 21 | 0.56 |
| 22 | 0.2275 |
| 23 | 0.477 |
| 24 | 0.1215 |
| 25 | 0.2257 |
| 26 | 0.2248 |
| 27 | 0.0347 |
| 28 | 0.0353 |
| 29 | 0.0077 |
| 30 | 0.0279 |
| 31 | 1.3116 |
| 32 | 0.0725 |
| 33 | 0.0151 |
| 34 | 0.0191 |
| 35 | 0.0082 |
| 36 | 0.0997 |
| 37 | 0.0337 |
| 38 | 0.0199 |
| 39 | 0.09 |

TABLE 5-continued

EC$_{1.5x}$ concentrations for SMN protein expression.

| Example | EC$_{1.5x}$ SMN protein (μM) |
|---|---|
| 40 | 0.0148 |
| 41 | 0.2068 |
| 42 | 0.0629 |
| 43 | 0.0562 |
| 44 | 0.2653 |
| 45 | 0.009 |
| 46 | 0.0314 |
| 47 | 0.0249 |
| 48 | 1.3205 |

TABLE 6

Maximum fold increase of SMN protein.

| Example | max. fold increase |
|---|---|
| 1 | 1.9 |
| 2 | 1.93 |
| 3 | 1.79 |
| 4 | 1.78 |
| 5 | 1.99 |
| 6 | 1.7 |
| 7 | 1.78 |
| 8 | 1.85 |
| 9 | 1.9 |
| 10 | 1.5 |
| 11 | 1.77 |
| 12 | 1.36 |
| 13 | 1.52 |
| 14 | 1.35 |
| 15 | 1.82 |
| 16 | 1.71 |
| 17 | 1.82 |
| 18 | 1.72 |
| 19 | 1.81 |
| 20 | 1.77 |
| 21 | 1.6 |
| 22 | 1.76 |
| 23 | 1.68 |
| 24 | 1.87 |
| 25 | 1.89 |
| 26 | 1.88 |
| 27 | 1.74 |
| 28 | 1.79 |
| 29 | 1.77 |
| 30 | 1.98 |
| 31 | 1.75 |
| 32 | 1.97 |
| 33 | 1.67 |
| 34 | 1.8 |
| 35 | 1.9 |
| 36 | 1.92 |
| 37 | 1.78 |
| 38 | 1.69 |
| 39 | 1.74 |
| 40 | 2.08 |
| 41 | 1.75 |
| 42 | 1.81 |
| 43 | 2.02 |
| 44 | 2.02 |
| 45 | 2.04 |
| 46 | 1.75 |
| 47 | 1.87 |
| 48 | 1.68 |

The invention claimed is:

1. A compound of formula (I):

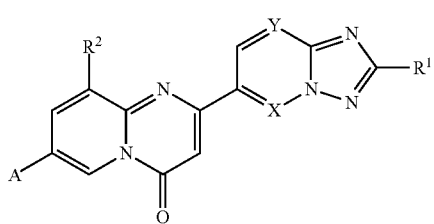

(I)

wherein

X is N and Y is $CR^3$ or X is $CR^4$ and Y is N;

$R^1$ is selected from hydrogen, cyano, halo, $C_{1-7}$-alkyl, $C_{1-7}$-haloalkyl, $C_{1-7}$-alkoxy or $C_{3-8}$-cycloalkyl;

$R^2$ is selected from hydrogen, cyano, halo, $C_{1-7}$-alkyl, $C_{1-7}$-haloalkyl, $C_{1-7}$-alkoxy or $C_{3-8}$-cycloalkyl;

$R^3$ is selected from hydrogen, cyano, halo, $C_{1-7}$-alkyl, $C_{1-7}$-haloalkyl, $C_{1-7}$-alkoxy or $C_{3-8}$-cycloalkyl;

$R^4$ is selected from hydrogen, cyano, halo, $C_{1-7}$-alkyl, $C_{1-7}$-haloalkyl, $C_{1-7}$-alkoxy or $C_{3-8}$-cycloalkyl;

A is N-heterocycloalkyl or $NR^5R^6$, wherein N-heterocycloalkyl comprises 1 or 2 nitrogen ring atoms and is optionally substituted with 1, 2, 3 or 4 substituents selected from $R^7$;

$R^5$ is heterocycloalkyl comprising 1 nitrogen ring atom, wherein heterocycloalkyl is optionally substituted with 1, 2, 3 or 4 substituents selected from $R^7$;

$R^6$ is hydrogen, $C_{1-7}$-alkyl or $C_{3-8}$-cycloalkyl;

$R^7$ is independently selected from $C_{1-7}$-alkyl, amino, amino-$C_{1-7}$-alkyl, $C_{3-8}$-cycloalkyl, heterocycloalkyl, and heterocycloalkyl-$C_{1-7}$-alkyl or two $R^7$ together form $C_{1-7}$-alkylene;

with the proviso that if A is N-heterocycloalkyl comprising only 1 nitrogen ring atom, then at least one $R^7$ substituent comprises a basic nitrogen;

or a pharmaceutically acceptable salt thereof.

2. A compound according to claim 1, wherein

X is N and Y is $CR^3$ or X is $CR^4$ and Y is N;

$R^1$ is $C_{1-7}$-alkyl;

$R^2$ is hydrogen or $C_{1-7}$-alkyl;

$R^3$ is hydrogen;

$R^4$ is hydrogen;

A is N-heterocycloalkyl, wherein N-heterocycloalkyl comprises 1 or 2 nitrogen ring atoms and is optionally substituted with 1 or 2 substituents selected from $R^7$;

R⁷ is independently selected from C₁₋₇-alkyl, amino, heterocycloalkyl, and heterocycloalkyl-C₁₋₇-alkyl, or two R⁷ together form C₁₋₇-alkylene;
with the proviso that if A is N-heterocycloalkyl comprising only 1 nitrogen ring atom, then at least one R⁷ substituent comprises a basic nitrogen;
or a pharmaceutically acceptable salt thereof.

3. A compound according to claim 1, wherein X is N and Y is CR³.

4. A compound according to claim 1, wherein X is CR⁴ and Y is N.

5. A compound according to claim 1, wherein R¹ is C₁₋₇-alkyl.

6. A compound according to claim 1, wherein R² is hydrogen or C₁₋₇-alkyl.

7. A compound of claim 1 of formula (I'):

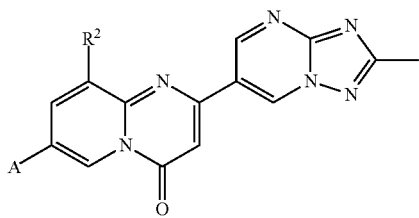

(I')

or a pharmaceutically acceptable salt thereof.

8. A compound of claim 1 of formula (I"):

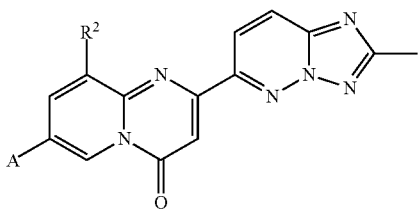

(I")

or a pharmaceutically acceptable salt thereof.

9. A compound according to claim 1, wherein A is NR⁵R⁶.

10. A compound according to claim 1, wherein A is a saturated mono-, bi- or tricyclic N-heterocycloalkyl comprising 1 or 2 nitrogen atoms and is optionally substituted with 1, 2, 3 or 4 substituents selected from R⁷.

11. A compound according to claim 1, wherein A is selected from the group of:

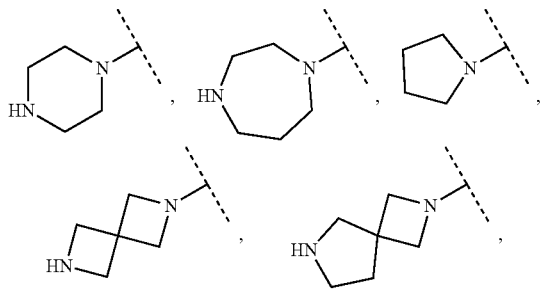

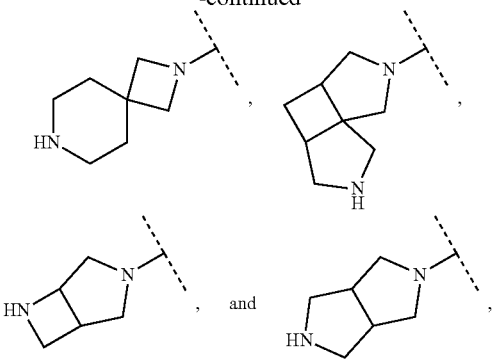

and wherein A is optionally substituted with 1 or 2 substituents selected from R⁷.

12. A compound according to claim 1, wherein each R⁷ is independently selected from C₁₋₇-alkyl, amino, heterocycloalkyl, and heterocycloalkyl-C₁₋₇-alkyl or two R⁷ together form C₁₋₇-alkylene.

13. A compound according to any of claims 1 to 12, wherein A is selected from:

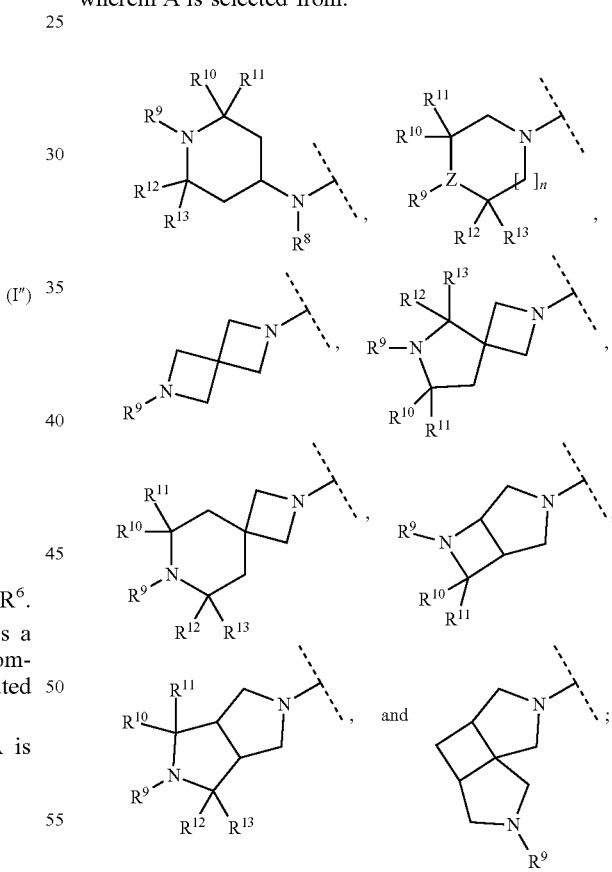

and wherein
Z is N or CH;
R⁸ is hydrogen, C₁₋₇-alkyl or C₃₋₈-cycloalkyl;
R⁹ is hydrogen, C₁₋₇-alkyl, amino, heterocycloalkyl, and heterocycloalkyl-C₁₋₇-alkyl, or —(CH₂)ₘ—NR¹⁴R¹⁵;
R¹⁰ is hydrogen or C₁₋₇-alkyl;
R¹¹ is hydrogen or C₁₋₇-alkyl;
R¹² is hydrogen or C₁₋₇-alkyl;
R¹³ is hydrogen or C₁₋₇-alkyl;

$R^{14}$ and $R^{15}$ are independently selected from hydrogen, $C_{1-7}$-alkyl and $C_{3-8}$-cycloalkyl;

n is 0, 1 or 2;

m is 0, 1, 2 or 3;

or $R^9$ and $R^{10}$ together form $C_{1-7}$-alkylene;
or $R^9$ and $R^{12}$ together form $C_{1-7}$-alkylene;
or $R^{10}$ and $R^{11}$ together form $C_{2-7}$-alkylene;
or $R^{10}$ and $R^{12}$ together form $C_{1-7}$-alkylene;
or $R^{10}$ and $R^{14}$ together form $C_{1-7}$-alkylene;
or $R^{12}$ and $R^{13}$ together form $C_{2-7}$-alkylene;
or $R^{12}$ and $R^{14}$ together form $C_{1-7}$-alkylene;
or $R^{14}$ and $R^{15}$ together form $C_{2-7}$-alkylene which is optionally substituted with alkoxy;

with the proviso that if Z is CH then $R^9$ is —$(CH_2)_m$—$NR^{14}R^{15}$; and with the proviso that if Z is N and $R^9$ is —$(CH_2)_m$—$NR^{14}R^{15}$ then m is 2 or 3.

14. A compound according to claim 13, wherein Z is N.

15. A compound according to claim 13, wherein $R^9$ and $R^{10}$ together form propylene.

16. A compound according to claim 13, wherein $R^{10}$ and $R^{11}$ together form ethylene.

17. A compound according to claim 1, wherein A is selected from the group of:

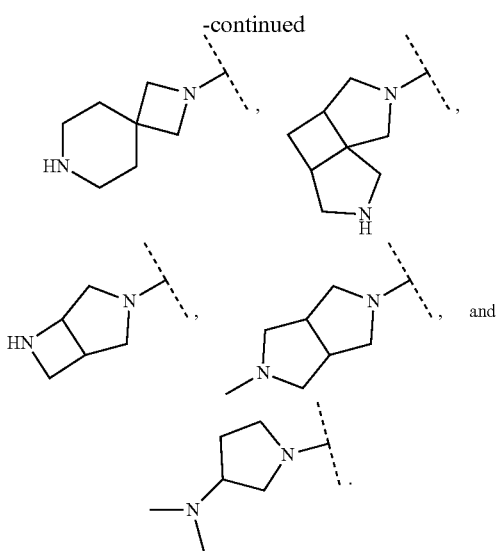

18. A compound according to claim 1 selected from the group consisting of:
- 2-(2-methyl-[1,2,4]triazolo[1,5-a]pyrimidin-6-yl)-7-piperazin-1-yl-pyrido[1,2-a]pyrimidin-4-one;
- 7-[(3R,5S)-3,5-dimethylpiperazin-1-yl]-2-(2-methyl-[1,2,4]triazolo[1,5-a]pyrimidin-6-yl)pyrido[1,2-a]pyrimidin-4-one;
- 7-[(3R)-3-(dimethylamino)pyrrolidin-1-yl]-2-(2-methyl-[1,2,4]triazolo[1,5-a]pyrimidin-6-yl)pyrido[1,2-a]pyrimidin-4-one;
- 7-(4-methyl-1,4-diazepan-1-yl)-2-(2-methyl-[1,2,4]triazolo[1,5-a]pyrimidin-6-yl)pyrido[1,2-a]pyrimidin-4-one;
- 7-(2,7-diazaspiro[3.5]nonan-2-yl)-2-(2-methyl-[1,2,4]triazolo[1,5-a]pyrimidin-6-yl)pyrido[1,2-a]pyrimidin-4-one;
- 7-(3,3-dimethylpiperazin-1-yl)-2-(2-methyl-[1,2,4]triazolo[1,5-a]pyrimidin-6-yl)pyrido[1,2-a]pyrimidin-4-one;
- 7-(2,6-diazaspiro[3.3]heptan-2-yl)-2-(2-methyl-[1,2,4]triazolo[1,5-a]pyrimidin-6-yl)pyrido[1,2-a]pyrimidin-4-one;
- 2-(2,8-7-(2-methyl-1,3,3a,4,6,6a-hexahydropyrrolo[3,4-c]pyrrol-5-yl)-2-(2-methyl-[1,2,4]triazolo[1,5-a]pyrimidin-6-yl)pyrido[1,2-a]pyrimidin-4-one;
- 7-(3,6-diazabicyclo[3.2.0]heptan-3-yl)-2-(2-methyl-[1,2,4]triazolo[1,5-a]pyrimidin-6-yl)pyrido[1,2-a]pyrimidin-4-one;
- 7-[4-(azetidin-3-yl)piperazin-1-yl]-2-(2-methyl-[1,2,4]triazolo[1,5-a]pyrimidin-6-yl)pyrido[1,2-a]pyrimidin-4-one;
- 7-[(3S,5S)-3,5-dimethylpiperazin-1-yl]-2-(2-methyl-[1,2,4]triazolo[1,5-a]pyrimidin-6-yl)pyrido[1,2-a]pyrimidin-4-one;
- 2-(2-methyl-[1,2,4]triazolo[1,5-a]pyrimidin-6-yl)-7-[4-(pyrrolidin-1-ylmethyl)-1-piperidyl]pyrido[1,2-a]pyrimidin-4-one;
- 7-(4,7-diazaspiro[2.5]octan-7-yl)-2-(2-methyl-[1,2,4]triazolo[1,5-a]pyrimidin-6-yl)pyrido[1,2-a]pyrimidin-4-one;
- 2-(2-methyl-[1,2,4]triazolo[1,5-a]pyrimidin-6-yl)-7-[4-(oxetan-3-yl)piperazin-1-yl]pyrido[1,2-a]pyrimidin-4-one;
- 9-methyl-2-(2-methyl-[1,2,4]triazolo[1,5-b]pyridazin-6-yl)-7-piperazin-1-yl-pyrido[1,2-a]pyrimidin-4-one;
- 7-[(3 S)-3-methylpiperazin-1-yl]-2-(2-methyl-[1,2,4]triazolo[1,5-a]pyrimidin-6-yl)pyrido[1,2-a]pyrimidin-4-one;
- 7-[(3R)-3-methylpiperazin-1-yl]-2-(2-methyl-[1,2,4]triazolo[1,5-b]pyridazin-6-yl)pyrido[1,2-a]pyrimidin-4-one;
- 7-[(3 S)-3-methylpiperazin-1-yl]-2-(2-methyl-[1,2,4]triazolo[1,5-a]pyrimidin-6-yl)pyrido[1,2-a]pyrimidin-4-one;
- 2-(2-methyl-[1,2,4]triazolo[1,5-b]pyridazin-6-yl)-7-piperazin-1-yl-pyrido[1,2-a]pyrimidin-4-one;
- 7-(4-methyl-1,4-diazepan-1-yl)-2-(2-methyl-[1,2,4]triazolo[1,5-b]pyridazin-6-yl)pyrido[1,2-a]pyrimidin-4-one;
- 7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one;
- 7-[(3R,5S)-3,5-dimethylpiperazin-1-yl]-2-(2-methyl-[1,2,4]triazolo[1,5-b]pyridazin-6-yl)pyrido[1,2-a]pyrimidin-4-one;
- 7-(4-methylpiperazin-1-yl)-2-(2-methyl-[1,2,4]triazolo[1,5-a]pyrimidin-6-yl)pyrido[1,2-a]pyrimidin-4-one;
- 7-[(3R)-3-methylpiperazin-1-yl]-2-(2-methyl-[1,2,4]triazolo[1,5-a]pyrimidin-6-yl)pyrido[1,2-a]pyrimidin-4-one;
- 9-methyl-7-(4-methyl-1,4-diazepan-1-yl)-2-(2-methyl-[1,2,4]triazolo[1,5-a]pyrimidin-6-yl)pyrido[1,2-a]pyrimidin-4-one;
- 7-[(3R,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;
- 9-methyl-7-(4-methylpiperazin-1-yl)-2-(2-methyl-[1,2,4]triazolo[1,5-b]pyridazin-6-yl)pyrido[1,2-a]pyrimidin-4-one;
- 7-(3,3-dimethylpiperazin-1-yl)-9-methyl-2-(2-methyl-[1,2,4]triazolo[1,5-b]pyridazin-6-yl)pyrido[1,2-a]pyrimidin-4-one;
- 7-[(3aS,6aR)-2-methyl-1,3,3a,4,6,6a-hexahydropyrrolo[3,4-c]pyrrol-5-yl]-9-methyl-2-(2-methyl-[1,2,4]triazolo[1,5-b]pyridazin-6-yl)pyrido[1,2-a]pyrimidin-4-one;
- 7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one;
- 9-methyl-2-(2-methyl-[1,2,4]triazolo[1,5-b]pyridazin-6-yl)-7-[4-(oxetan-3-yl)piperazin-1-yl]pyrido[1,2-a]pyrimidin-4-one;
- 7-(4-ethylpiperazin-1-yl)-9-methyl-2-(2-methyl-[1,2,4]triazolo[1,5-b]pyridazin-6-yl)pyrido[1,2-a]pyrimidin-4-one;
- 7-(2-methyl-1,3,3a,4,6,6a-hexahydropyrrolo[3,4-c]pyrrol-5-yl)-2-(2-methyl-[1,2,4]triazolo[1,5-b]pyridazin-6-yl)pyrido[1,2-a]pyrimidin-4-one;
- 7-[(8aR)-3,4,6,7,8,8a-hexahydro-1H-pyrrolo[1,2-a]pyrazin-2-yl]-9-methyl-2-(2-methyl-[1,2,4]triazolo[1,5-b]pyridazin-6-yl)pyrido[1,2-a]pyrimidin-4-one;
- 7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one;
- 7-[(8aR)-3,4,6,7,8,8a-hexahydro-1H-pyrrolo[1,2-a]pyrazin-2-yl]-2-(2-methyl-[1,2,4]triazolo[1,5-b]pyridazin-6-yl)pyrido[1,2-a]pyrimidin-4-one;
- 7-[(3S,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-2-(2-methyl-[1,2,4]triazolo[1,5-b]pyridazin-6-yl)pyrido[1,2-a]pyrimidin-4-one;

7-(4-methylpiperazin-1-yl)-2-(2-methyl-[1,2,4]triazolo[1,5-b]pyridazin-6-yl)pyrido[1,2-a]pyrimidin-4-one;

9-methyl-7-[(3R)-3-methylpiperazin-1-yl]-2-(2-methyl-[1,2,4]triazolo[1,5-b]pyridazin-6-yl)pyrido[1,2-a]pyrimidin-4-one;

7-[(3R)-3-(dimethylamino)pyrrolidin-1-yl]-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-2-(2-methyl-[1,2,4]triazolo[1,5-b]pyridazin-6-yl)pyrido[1,2-a]pyrimidin-4-one;

7-(4-ethylpiperazin-1-yl)-2-(2-methyl-[1,2,4]triazolo[1,5-b]pyridazin-6-yl)pyrido[1,2-a]pyrimidin-4-one;

7-(4,7-diazaspiro[2.5]octan-7-yl)-2-(2-methyl-[1,2,4]triazolo[1,5-b]pyridazin-6-yl)pyrido[1,2-a]pyrimidin-4-one;

9-methyl-7-[(3S)-3-methylpiperazin-1-yl]-2-(2-methyl-[1,2,4]triazolo[1,5-b]pyridazin-6-yl)pyrido[1,2-a]pyrimidin-4-one;

7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one;

7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one; and 7-(2,7-diazaspiro[3.4]octan-2-yl)-9-methyl-2-(2-methyl-[1,2,4]triazolo[1,5-b]pyridazin-6-yl)pyrido[1,2-a]pyrimidin-4-one;

or a pharmaceutically acceptable salt thereof.

19. A compound according to claim 1, selected from the group consisting of:

7-(2,7-diazaspiro[3.5]nonan-2-yl)-2-(2-methyl-[1,2,4]triazolo[1,5-a]pyrimidin-6-yl)pyrido[1,2-a]pyrimidin-4-one;

2-(2-methyl-[1,2,4]triazolo[1,5-b]pyridazin-6-yl)-7-piperazin-1-yl-pyrido[1,2-a]pyrimidin-4-one;

7-(3,3-dimethylpiperazin-1-yl)-9-methyl-2-(2-methyl-[1,2,4]triazolo[1,5-b]pyridazin-6-yl)pyrido[1,2-a]pyrimidin-4-one;

7-[(3aS,6aR)-2-methyl-1,3,3a,4,6,6a-hexahydropyrrolo[3,4-c]pyrrol-5-yl]-9-methyl-2-(2-methyl-[1,2,4]triazolo[1,5-b]pyridazin-6-yl)pyrido[1,2-a]pyrimidin-4-one;

7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one;

7-(4-ethylpiperazin-1-yl)-9-methyl-2-(2-methyl-[1,2,4]triazolo[1,5-b]pyridazin-6-yl)pyrido[1,2-a]pyrimidin-4-one;

7-(2-methyl-1,3,3a,4,6,6a-hexahydropyrrolo[3,4-c]pyrrol-5-yl)-2-(2-methyl-[1,2,4]triazolo[1,5-b]pyridazin-6-yl)pyrido[1,2-a]pyrimidin-4-one;

7-[(8aR)-3,4,6,7,8,8a-hexahydro-1H-pyrrolo[1,2-a]pyrazin-2-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-9-methyl-2-(2-methyl-[1,2,4]triazolo[1,5-b]pyridazin-6-yl)pyrido[1,2-a]pyrimidin-4-one;

7-(2,7-diazaspiro[3.5]nonan-2-yl)-2-(2-methyl-[1,2,4]triazolo[1,5-b]pyridazin-6-yl)pyrido[1,2-a]pyrimidin-4-one;2,2,2-trifluoroacetic acid;

9-methyl-7-[(3R)-3-methylpiperazin-1-yl]-2-(2-methyl-[1,2,4]triazolo[1,5-b]pyridazin-6-yl)pyrido[1,2-a]pyrimidin-4-one;

7-[(3S,5S)-3,5-dimethylpiperazin-1-yl]-2-(2-methyl-[1,2,4]triazolo[1,5-b]pyridazin-6-yl)pyrido[1,2-a]pyrimidin-4-one;

7-(4-ethylpiperazin-1-yl)-2-(2-methyl-[1,2,4]triazolo[1,5-b]pyridazin-6-yl)pyrido[1,2-a]pyrimidin-4-one;

7-(4,7-diazaspiro[2.5]octan-7-yl)-2-(2-methyl-[1,2,4]triazolo[1,5-b]pyridazin-6-yl)pyrido[1,2-a]pyrimidin-4-one;

9-methyl-7-[(3S)-3-methylpiperazin-1-yl]-2-(2-methyl-[1,2,4]triazolo[1,5-b]pyridazin-6-yl)pyrido[1,2-a]pyrimidin-4-one;

7-(6-methyl-2,6-diazaspiro[3.3]heptan-2-yl)-2-(2-methyl-[1,2,4]triazolo[1,5-b]pyridazin-6-yl)pyrido[1,2-a]pyrimidin-4-one; and 7-((3aR,4aR,7aS)-hexahydro-1H-cyclobuta[1,2-c:1,4-c']dipyrrol-2(3H)-yl)-2-(2-methyl-[1,2,4]triazolo[1,5-b]pyridazin-6-yl)-4H-pyrido[1,2-a]pyrimidin-4-one;

or a pharmaceutically acceptable salt thereof.

20. A pharmaceutical composition comprising a compound of formula (I) according to claim 1, or a pharmaceutically acceptable salt thereof, and one or more pharmaceutically acceptable excipients.

21. A method for the treatment of spinal muscular atrophy in a human, which method comprises administering a therapeutically effective amount of a compound of formula (I) according to claim 1, or a pharmaceutically acceptable salt thereof, to a human in need of such treatment.

22. A compound of claim 1, wherein the compound is 2-(2-methyl-[1,2,4]triazolo[1,5-a]pyrimidin-6-yl)-7-piperazin-1-yl-pyrido[1,2-a]pyrimidin-4-one, or a pharmaceutically acceptable salt thereof.

23. A compound of claim 1, wherein the compound is 7-[(3R,5S)-3,5-dimethylpiperazin-1-yl]-2-(2-methyl-[1,2,4]triazolo[1,5-a]pyrimidin-6-yl)pyrido[1,2-a]pyrimidin-4-one, or a pharmaceutically acceptable salt thereof.

24. A compound of claim 1, wherein the compound is 7-(2,7-diazaspiro[3.5]nonan-2-yl)-2-(2-methyl-[1,2,4]triazolo[1,5-a]pyrimidin-6-yl)pyrido[1,2-a]pyrimidin-4-one, or a pharmaceutically acceptable salt thereof.

25. A compound of claim 1, wherein the compound is 7-(3,6-diazabicyclo[3.2.0]heptan-3-yl)-2-(2-methyl-[1,2,4]triazolo[1,5-a]pyrimidin-6-yl)pyrido[1,2-a]pyrimidin-4-one, or a pharmaceutically acceptable salt thereof.

26. A compound of claim 1, wherein the compound is 7-[(3R)-3-(dimethylamino)pyrrolidin-1-yl]-9-methyl-2-(2-methyl-[1,2,4]triazolo[1,5-b]pyridazin-6-yl)pyrido[1,2-a]pyrimidin-4-one, or a pharmaceutically acceptable salt thereof.

27. A compound of claim 1, wherein the compound is 7-(4-ethylpiperazin-1-yl)-9-methyl-2-(2-methyl-[1,2,4]triazolo[1,5-b]pyridazin-6-yl)pyrido[1,2-a]pyrimidin-4-one, or a pharmaceutically acceptable salt thereof.

28. A compound of claim 1, wherein the compound is 7-(2,7-diazaspiro[3.5]nonan-2-yl)-9-methyl-2-(2-methyl-[1,2,4]triazolo[1,5-b]pyridazin-6-yl)pyrido[1,2-a]pyrimidin-4-one, or a pharmaceutically acceptable salt thereof.

29. A compound of claim 1, wherein the compound is 7-[(8aR)-3,4,6,7,8,8a-hexahydro-1H-pyrrolo[1,2-a]pyrazin-2-yl]-2-(2-methyl-[1,2,4]triazolo[1,5-b]pyridazin-6-yl)pyrido[1,2-a]pyrimidin-4-one, or a pharmaceutically acceptable salt thereof.

30. A compound of claim 1, wherein the compound is 9-methyl-7-[(3R)-3-methylpiperazin-1-yl]-2-(2-methyl-[1, 2,4]triazolo[1,5-b]pyridazin-6-yl)pyrido[1,2-a]pyrimidin-4-one, or a pharmaceutically acceptable salt thereof.

31. A compound of claim 1, wherein the compound is 7-(4-ethylpiperazin-1-yl)-2-(2-methyl-[1,2,4]triazolo[1,5-b]pyridazin-6-yl)pyrido[1,2-a]pyrimidin-4-one, or a pharmaceutically acceptable salt thereof.

32. A compound of claim 1, wherein the compound is 7-(4,7-diazaspiro[2.5]octan-7-yl)-2-(2-methyl-[1,2,4]triazolo[1,5-b]pyridazin-6-yl)pyrido[1,2-a]pyrimidin-4-one, or a pharmaceutically acceptable salt thereof.

33. A compound of claim 1, wherein the compound is 9-methyl-7-[(3 S)-3-methylpiperazin-1-yl]-2-(2-methyl-[1,2,4]triazolo[1,5-b]pyridazin-6-yl)pyrido[1,2-a]pyrimidin-4-one, or a pharmaceutically acceptable salt thereof.

* * * * *